(12) United States Patent
Klipstein et al.

(10) Patent No.: US 7,214,952 B2
(45) Date of Patent: May 8, 2007

(54) LED LAMPS AND LED DRIVER CIRCUITS FOR THE SAME

(75) Inventors: Donald J. Klipstein, Upper Darby, PA (US); Jack Brass, Toronto (CA)

(73) Assignee: Brasscorp Limited (CA)

( * ) Notice: Subject to any disclaimer, the term of this patent is extended or adjusted under 35 U.S.C. 154(b) by 122 days.

(21) Appl. No.: 10/885,031

(22) Filed: Jul. 7, 2004

(65) Prior Publication Data

US 2005/0007777 A1 Jan. 13, 2005

Related U.S. Application Data

(60) Provisional application No. 60/521,276, filed on Mar. 24, 2004, provisional application No. 60/481,986, filed on Feb. 1, 2004, provisional application No. 60/481,062, filed on Jul. 7, 2003.

(51) Int. Cl.
*H05B 33/00* (2006.01)
*G01N 21/33* (2006.01)

(52) U.S. Cl. .............................. 250/504 H; 250/504 R; 250/455.11; 250/493.1; 250/365; 362/244

(58) Field of Classification Search ............ None
See application file for complete search history.

(56) References Cited

U.S. PATENT DOCUMENTS 3,808,434 A 4/1974 Gutbier (Continued)

FOREIGN PATENT DOCUMENTS

CA 2200364 5/1997

(Continued)

OTHER PUBLICATIONS

Johnson, Craig, Infinity Task Light, The Punishment Zone, The LED Museum, Jun. 24, 2002, Seattle, USA, http://ledmuseum.home.att.net/inf1.htm.

(Continued)

*Primary Examiner*—Nikita Wells
(74) *Attorney, Agent, or Firm*—Katten Muchin Rosenman LLP

(57) ABSTRACT

LED lamp has LEDs aimed rearwards with either a concave mirror to the rear of each LED, or one concave mirror to the rear of two or more LEDs, collecting the light from the LEDs to form a forward projecting beam. LEDs may be high power types that require heatsinking. LED lamp may have a lens forward of each LED to collimate the radiation produced by the LEDs into a beam, where at least one lens has at least one aspheric curved surface. LED lamp may have a transparent reflective optic to collimate the radiation produced by each LED into a beam. For an inspection lamp, the LEDs typically have a peak wavelength of 395 to 415 naometers for seeing the area being irradiated but not so visible as to overwhelm fluorescence of fluorescent materials to be detected. Other wavelengths may be used. LED inspection lamp has a combination of LEDs of different wavelengths or a combination of at least one LED and at least one other light source such that the lamp produces radiation suitable for detection of materials to be detected and adequately illuminates the area being irradiated. LED lamp has LEDs that produce a beam of suitable radiation with a width of 10 degrees or less without additional optics. LED inspection lamp has head attached to a flexible member, with head serving as heatsink for one or more high power LEDs. Current regulator circuits are also disclosed.

25 Claims, 18 Drawing Sheets

U.S. PATENT DOCUMENTS

| | | | |
|---|---|---|---|
| 4,185,891 | A | 1/1980 | Kaestner |
| 4,826,269 | A | 5/1989 | Streifer et al. |
| 4,963,798 | A | 10/1990 | McDermott |
| 5,092,331 | A | 3/1992 | Nakamura et al. |
| 5,749,830 | A | 5/1998 | Kaneko et al. |
| 5,785,404 | A | 7/1998 | Wiese |
| 5,806,961 | A | 9/1998 | Dalton et al. |
| 5,954,206 | A | 9/1999 | Mallon et al. |
| 5,975,712 | A | 11/1999 | Shiao |
| 5,984,861 | A | 11/1999 | Crowley |
| 6,095,661 | A | 8/2000 | Lebens et al. |
| 6,142,650 | A | 11/2000 | Brown et al. |
| D434,868 | S | 12/2000 | Trigiani |
| 6,183,086 | B1 | 2/2001 | Neubert |
| 6,190,020 | B1 | 2/2001 | Hartley |
| 6,200,134 | B1 | 3/2001 | Kovac et al. |
| 6,250,771 | B1 | 6/2001 | Sharrah et al. |
| 6,305,818 | B1 | 10/2001 | Lebens et al. |
| 6,468,077 | B1 | 10/2002 | Melikechi et al. |
| 6,485,160 | B1 | 11/2002 | Sommers et al. |
| 6,491,408 | B1 | 12/2002 | Cooper et al. |
| 6,590,220 | B1 | 7/2003 | Kalley et al. |
| 6,710,363 | B1 * | 3/2004 | Trigiani .................. 250/504 H |
| 2002/0191396 | A1 | 12/2002 | Reiff et al. |
| 2003/0098425 | A1 | 5/2003 | Sosinsky |
| 2003/0123254 | A1 | 7/2003 | Brass et al. |
| 2004/0223342 | A1 * | 11/2004 | Klipstein et al. ........... 362/555 |

FOREIGN PATENT DOCUMENTS

| | | |
|---|---|---|
| CA | 2200365 | 5/1997 |
| CA | 2284870 | 9/1998 |
| CA | 2280398 | 4/2000 |
| CA | 2405802 | 10/2001 |
| DE | DT 25 42 220 A1 | 3/1977 |
| DE | DD 299 574 A5 | 4/1992 |
| DE | 200 21 934 U1 | 4/2001 |
| DE | 201 10 813 U1 | 9/2001 |
| EP | 0 523 927 A2 | 1/1993 |
| EP | 1 059 202 A2 | 12/2000 |
| GB | 810256 | 3/1959 |
| WO | WO 98/39636 | 9/1998 |
| WO | WO 99/35486 | 7/1999 |
| WO | WO 01 52605 A2 | 7/2001 |
| WO | WO 01 81973 A1 | 11/2001 |
| WO | WO 03/004929 A1 | 1/2003 |
| WO | WO 03/004932 A1 | 1/2003 |

OTHER PUBLICATIONS

Craig Johnson, LEDTronics FlashLED, The LED Museum, pre-Sep. 4, 2000, http://ledmuseum.home.att.net/tronics.htm.

Hi-Power FlashLED(R) Flashlights, LEDTronics, Inc., date unknown, http://netdisty.net/ds/flt-3001/default.asp.

Osram Sylvania, Preliminary data sheet for OS-WL01A, dated Feb. 25, 2000, pp. 4.

LED Museum at http://ledmuseum.home.att.net/ledleft.htm printed Feb. 27, 2002.

Product pages for Dorcy "Cool Blue" at http://www.dorcy.com/led%20new.htm printed Feb. 27, 2002.

Safety LED Hi-power FlashLED Flashlights at http:// secure.implex.net/NBAComputers/browse.cfm?CategoryID=8 printed Dec. 10, 2001.

Review of LEDTronics Mini-FlashLED at http://ledmuseum.home.att.net/flashled.htm printed Dec. 10, 2001.

Michael Sayer et al. Measurement, Instrumentation and Experiment Design in Physics and Engineering. Prentice-Hall of India. New Delhi, 2000, pp. 197-198. (ISBN 81-203-1269-4).

Lewis R. Koller. Ultraviolet Radiation. (2nd ed.) John Wiley & Sons, New York, 1965, pp. 158-181.

Primalec, Invictalux, Aug. 18, 2006, Kent, UK, http://www.primalec.co.uk/products/ultra/Invictalux.html.

Primalec, Invictalux, Mar. 3, 2003, Kent, UK.

* cited by examiner

LED LAMPS AND LED DRIVER CIRCUITS FOR THE SAME

CROSS-REFERENCE TO RELATED APPLICATIONS

This application claims the benefit of the filing date of U.S. Provisional Patent Application No. 60/481,062 filed 7 Jul. 2003 under the title LED INSPECTION LAMP AND LED DRIVER CIRCUIT FOR USE IN THE SAME; U.S. Provisional Patent Application No. 60/481,986 filed 1 Feb. 2004 under the title LED INSPECTION LAMP AND DRIVER CIRCUITRY FOR THE SAME; and U.S. Provisional Patent Application No. 60/521,276 filed 24 Mar. 2004 under the title LED INSPECTION LAMPS AND LED DRIVER CIRCUITS FOR THE SAME. The content of the above Provisional Patent Applications is hereby expressly incorporated by reference into the detailed description of hereof.

FIELD OF THE INVENTION

This invention is related to the general field of LED lamps, and in particular to the structure and driving circuitry for such lamps, and to such lamps for inspection (non-destructive testing).

BACKGROUND OF INVENTION

LED lamps are known. For example, inspection lamps that cause fluorescence of fluorescent materials are widely used for detection of fluorescent materials. For example, fluids that are under pressure can include fluorescent dyes; so that, leaks of such fluids can be detected by illuminating the leaking fluids with such inspection lamps.

One common application of inspection lamps is detection of leaks of the refrigerant in automotive air conditioning systems. Fluorescent dyes that are mixed with the lubricant that is present in automotive air conditioning systems typically visibly fluoresce when illuminated with blue, violet or near-ultraviolet wavelengths. Inspection lamps that would be used for detecting leaks of such fluids would produce blue, violet or near-ultraviolet wavelengths.

In the past, such inspection lamps used incandescent, halogen, or mercury vapor light sources. Now that LEDs that produce the useful wavelengths are available, inspection lamps can be made that are smaller and lighter, have less power consumption, and produce less heat than inspection lamps without LEDs. Furthermore, inspection lamps with incandescent, halogen or mercury vapor light sources required filters to remove undesired visible wavelengths that interfere with seeing the fluorescence of visible materials, while LEDs often produce little enough of undesired wavelengths to not require filters.

It has been found that wavelengths in or near the range of 395–415 nanometers are useful for searching for small quantities of visibly fluorescent materials since wavelengths of 395–415 nanometers are slightly visible. If the light from an inspection lamp is slightly visible, this helps in seeing what is being irradiated with the inspection lamp. Wavelengths longer than 415 nanometers are more visible than shorter wavelengths and typically require the user of the inspection lamp to wear glasses that attenuate or block the visible wavelengths that are produced by the inspection lamp.

Alternatively, inspection lamps that produce wavelengths near 450 nanometers have been found to be useful for some purposes. For example, fluorescent dyes that are added to some oils and automotive fluids do not respond as well to violet and some near-ultraviolet wavelengths as they do to blue wavelengths. As another example, some body fluids weakly fluoresce from both ultraviolet and visible wavelengths, while many fabrics fluoresce from ultraviolet and violet wavelengths but not blue wavelengths longer than approx. 420 nanometers. As a result, police officers searching for body fluids would use blue inspection lamps that cause fluorescence of said body fluids but not of fluorescent fabrics. Typically, inspection lamps that produce blue wavelengths such as 450 nanometers would be used with glasses that block the visible wavelengths produced by such inspection lamps.

While LED lamps, such as LED inspection lamps, already exist, they can be improved upon.

SUMMARY OF INVENTION

The present invention provides LED inspection lamps that are suitable for causing fluorescent materials to fluoresce to assist in the detection of such fluorescent materials. Said inspection lamps have one or more LEDs that typically have a peak wavelength of 395 to 415 nanometers, although other wavelengths can be found useful for such a purpose or for other purposes.

LEDs used in such inspection lamps may or may not be high power LEDs that require heatsinking. The present invention provides any necessary heatsinking. Any embodiment of the present invention may have a thermal cutout device.

In a first aspect, the present invention is an inspection lamp having one or more LEDs aimed generally forwards and producing radiation that is collimated into a beam by a concave mirror associated with each of the one or more LEDs.

In a second aspect, the present invention is an LED inspection lamp having one or more LEDs aimed rearwards with a concave mirror behind each of said one or more LEDs in order to collimate the radiation from said one or more LEDs into a beam. The concave mirror to the rear of each of said one or more LEDs may have a paraboloidal reflective surface, an ellipsoidal reflective surface, a spherical reflective surface, or a different shape reflective surface. An LED may be placed in a position forward of the concave mirror so as to produce as intense a beam as possible, so as to produce a beam that has an attractive appearance, so as to image the LED chip, or so as to image another part of the LED. Other positions of the LED with respect to the concave mirror may be used. A sheet of opaque material with a hole in it may be placed forward of the LED or around of the tip of the LED and the mirror may form an image of the hole in order to produce a beam with a sharp edge.

In a variation of this second aspect, the present invention has a single concave mirror to collimate into a beam the radiation produced by two or more LEDs that are aimed generally rearwards.

In a third aspect, the present invention is an LED inspection lamp having one or more LEDs aimed forwards and a lens forward of each of said one or more LEDs in order to collimate the radiation from said one or more LEDs into a beam. The lens forward from each of said one or more LEDs has at least one aspheric curved surface so as to collimate the radiation into a better beam than is available using a spherical curved lens surface. Such an aspheric lens surface curve may be paraboloidal, ellipsoidal, a combination of paraboloidal and spherical, a combination of paraboloidal and ellipsoidal, or a different curve. The LEDs may be directly rearward of the axes of their respective lenses. LEDs that are not on the central axis of the head section of the inspection lamp may be placed further from the central axis of the head section of the inspection lamp than the axes of their respective lenses are so that the beams formed by the lenses converge at a finite distance from the lenses. The LEDs may be placed rearward of the lenses such that the lenses image the chips of the LEDs, such that the lenses image the front surfaces of the LEDs, or a different position of the LEDs may be found suitable. A sheet of opaque material with a hole may be placed around the tip of each LED or forward of each LED and a lens forward of each said hole may form a beam that is an image of said hole in order to produce a beam with a sharp edge.

In a fourth aspect, the present invention is an inspection lamp having one or more LEDs, wherein the LEDs produce radiation that is collimated into a beam by transparent optics that have total internal reflection.

In a fifth aspect, the present invention is an inspection lamp that has at least one LED that produces essentially invisible radiation that is suitable for causing fluorescence of fluorescent materials, and at least one other light source that produces visible light that illuminates the area being illuminated.

In a sixth aspect, the present invention is an inspection lamp having at least one LED that produces radiation that is suitable for causing fluorescence of fluorescent materials, wherein the at least one LED produces a beam of such radiation 10 degrees wide or narrower without requiring additional optics.

In a seventh aspect, the present invention is an LED inspection lamp with a distinct head and handle connected to each other by a flexible member, wherein the head contains at least one LED and wherein the head or other parts of the inspection lamp serve as heatsinking for the one or more LEDs.

Optical surfaces of any lenses or any mirors or reflectors or other optics used in the present invention may or may not be faceted. Optical surfaces of any lenses or any mirrors or reflectors or other optics used in the present invention may or may not be textured. Any lenses may be translucent, frosted or textured for purposes such as achieving diffusion. Any embodiment of the present invention may have a filter to remove some wavelengths of radiation produced by any LEDs in the present invention. Any such filter may be dye based, dichroic, or of an interference type or colloidal type or of any other type.

In any of these aspects the inspection lamp may have a current regulator circuit to control the magnitude of the current flowing through the one or more LEDs. The current regulator circuit may be a switching current regulator. The current regulator circuit may be a boost converter circuit that includes current regulating means. The current regulator circuit may include a diode that protects the circuit from any accidental connecing of a battery having reversed polarity.

In any aspect the inspection lamp may include indicator lamps such as a battery status indicator lamp. In any aspect the inspection lamp may have a switch. The switch may be a momentary switch, a non-momentary switch, or a switch that can be used as a momentary switch and as a non-momentary switch.

In any aspect the present invention may further comprise a charging jack for recharging of any rechargeable batteries. In any aspect the present invention may further comprise charging circuitry or a charger.

In any aspect the invention may further comprise means to achieve strobing any LEDs.

DETAILED DESCRIPTION OF THE PREFERRED EMBODIMENTS

Throughout this specification a light emitting diode may be referred to as an LED. It is to be noted that numerous components are similar for different embodiments described herein, and components from one embodiment can be used on other embodiments. The description for similar components in different embodiments applies equally to all embodiments unless the context specifically requires otherwise. Components from one embodiment can be applied to other embodiments unless the context specifically requires otherwise, and specific reference to the croos-application of such components will not be made for each embodiment, but is expressly stated hereby.

Figure 1:
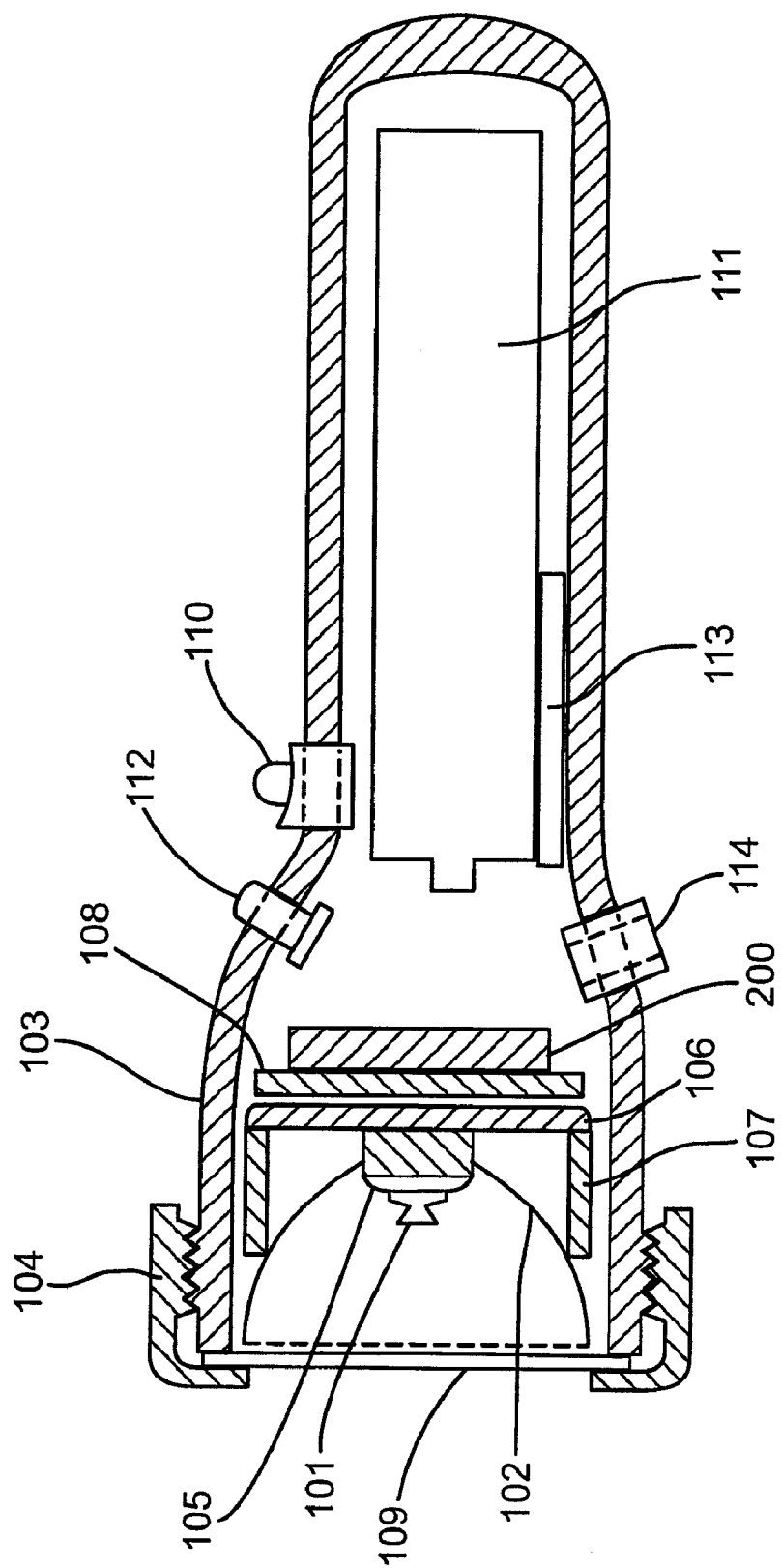
FIG. 1 is a cross sectional side view of a first embodiment of the present invention.

Referring to FIG. 1, a preferred embodiment of the present invention is an inspection lamp 100 that resembles a flashlight. It has a housing 103, a retainer ring 104 and a window 109.

The light source is an LED 101. In the preferred embodiment of the invention, the LED is a side emitter high power type that radiates mainly into directions within 40 degrees of a plane which the axis of the LED is normal to. Radiation in said directions is utilized well by the reflector 102. In the preferred embodiment of the present invention, the reflector 102 is paraboloidal (parabolic) in shape. It can be ellipsoidal in shape instead of paraboloidal in order to best direct the radiation from the LED 101 onto a target that is a finite distance forward of the inspection lamp 100. Other reflector shapes may be found usable for the present invention whether or not such alternative reflector shapes are theoretically ideal for the purpose.

The LED 101 normally requires a heat sink, which may comprise a disk or cylinder 105, which would be attached to a circular plate 106, which would be attached to a short tube 107. Alternative heat sinking arrangements may be used. For example, it may be feasible to omit the cylinder or disc 105 depending on the geometry of the reflector 102. The cylinder or disc 105 and the circular plate 106 may be comprised in a single piece of metal. The cylinder 107 may be omitted in forseeable embodiments of the present invention. One or more metal rods or metal bars may be attached to the circular plate 108 and extend rearward to assist removal of heat from the circular plate 108. It is forseeable that embodiments of the present invention may have a variation of the LED 101 that includes a heat sink.

Electrical connections in the inspection lamp 100 are not shown but will be evident to those skilled in the art of building flashlights and inspection lamps.

The preferred embodiment of the present invention has a battery 111, a power switch 110, and a circuit board 108 that has a boost converter circuit 200. The boost converter circuit 200 is necessary for the battery 111 to power the LED 101 since the voltage required to operate the LED 101 is greater than that supplied by the battery 101.

It is forseeable that alternative embodiments of the present invention can have a battery 111 that has a voltage great enough to operate the LED 101. In such a case, the boost converter circuit 200 is not necessary. Typically but not necessarily in such a case, in lieu of the boost converter circuit 200 a resistor or a current regulator would be used. Such a current regulator may be a switching regulator.

In the preferred embodiment of the present invention, the battery 111 is rechargeable. A charging circuit board 113 and a charging jack 114 are provided so that the battery 111 can be recharged without removing it. An indicator lamp 112 is provided and connected to the charging circuit board 113 to indicate the charge status of the battery 111. The indicator lamp 112 is optional. It is to be noted that some of the connections have been omitted from the FIG. in order to aid in the overall clarity of the FIG. Other embodiments of the present invention can have the battery 111 recharged with an external charger that does not require the charging circuit board 111. In other embodiments of the present invention the battery 111 may be removed for recharging or may be of a non-rechargeable type that must be replaced when it is depleted. Alternative embodiments of the present invention may receive power from a power source other than a battery inside the housing 103.

In the preferred embodiment of the present invention, the housing 103 comprises a head section 103a and a handle section 103b and is a single piece of plastic. In other embodiments of the present invention, the housing 103 may comprise more than one piece. Part or all of the housing 103 may be of a material other than plastic. Part or all of the housing 103 may be metal. Part or all of the housing 103 may be metal for heat sinking purposes. A part of the handle section 103b may be enclosed in rubber or some other non-conductive material to provide a grip surface.

Alternative optical schemes are possible. As an example, the reflector 102 may be designed or positioned such that a lens is required forward of the inspection lamp 100 for best results.

Accessories may be provided with the inspection lamp 100. Such accessories may or may not be removable from the inspection lamp 100 and may include and are not necessarily limited to any combination of the following:

a) a close-up lens to focus the beam produced by the inspection lamp 100 into a concentrated spot at a finite distance forward of the inspection lamp 100.

b) a different optical accessory such as means to widen the beam.

c) a beam focusing adjustment, such as means to move the LED 101 or the reflector 102 or an adjustable lens arrangement forward of the reflector 102.

d) waterproofing means.

e) means to attach a lanyard to the inspection lamp 100.

Figure 2:
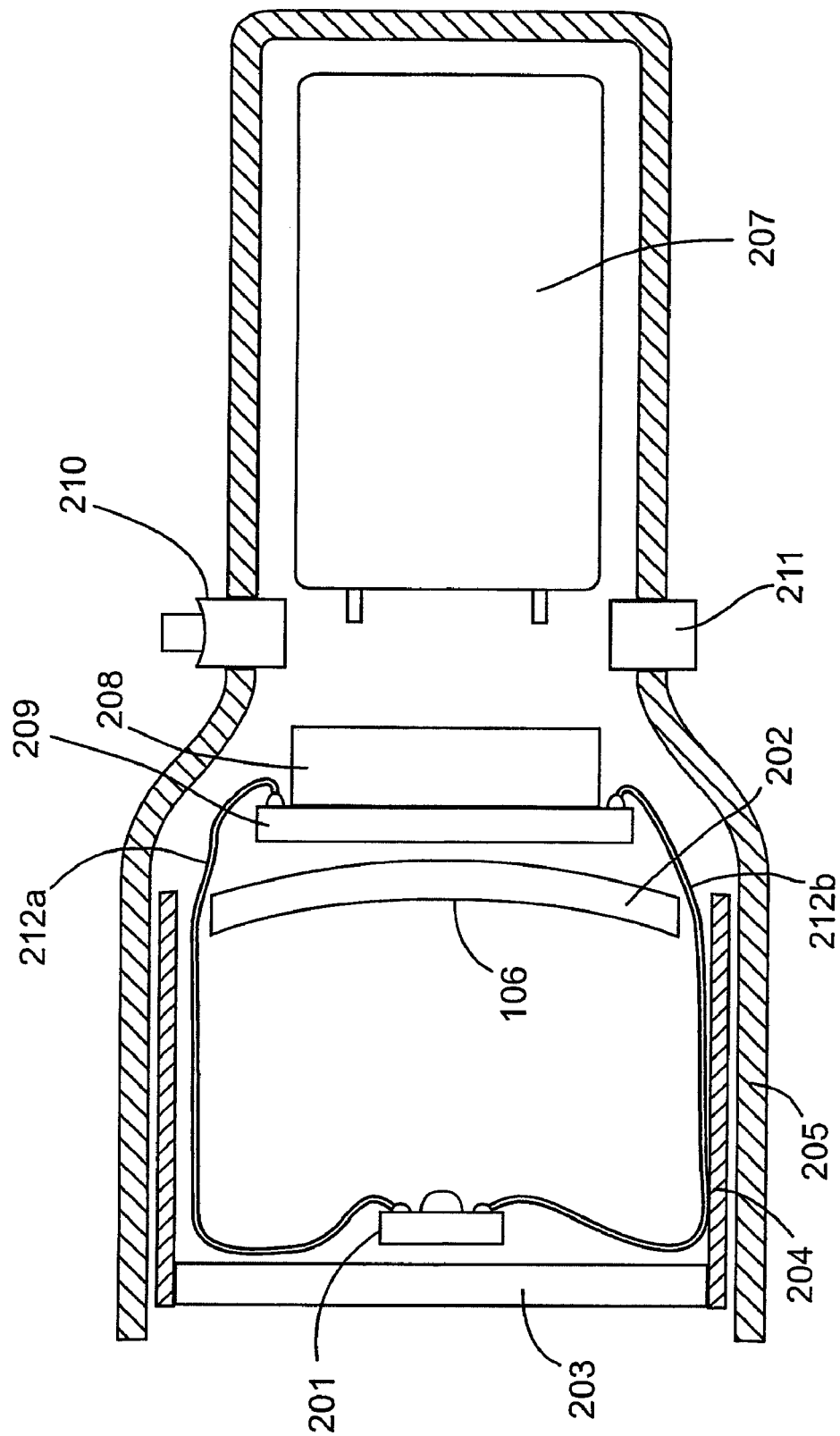
FIG. 2 is a cross sectional side view of a second embodiment of the present invention.

Referring to FIG. 2, a second embodiment of the present invention 200 is an inspection lamp that resembles a flashlight. An LED 201 is provided as a source of radiation that is suitable for causing fluorescence of fluorescent materials. The LED is typically a high power type that typically requires heatsinking. The radiation from the LED may be mainly of wavelengths in a narrow spectral band that peaks in the range of 395 to 415 nanometers, so that the beam produced by the inspection lamp 200 is slightly visible but not so visible as to interfere with viewing of any fluorescent material that the inspection lamp 200 would be used to detect. Longer wavelengths will be found to be better for some purposes, but longer wavelengths would typically necessitate use of a viewing filter or viewing glasses that block at least most of the visible radiation produced by the LED 201. It is forseeable that in some applications it would be desirable to use a viewing filter that blocks at least some of the exciting wavelengths even if the exciting radiation has a peak wavelength of 415 nanometers or less. Wavelengths shorter than 395 nanometers may be used where required to produce fluorescence of materials that require such shorter wavelengths to produce useful fluorescence, or where the visibility of 395–415 nanometers is excessive. The LED 201 is aimed rearwards and typically has a wide or moderately wide radiation pattern that is easy to collimate into a beam by means of a concave mirror 202. As an example, the LED 201 may be a Lumileds "Luxeon", one of Nichia's heatsinkable high power UV LEDs such as NCCU001E or NCCU033E, or heatsinkable LEDs by ISP. The LED 201 may alternatively be a lower power type that is sometimes known as a "high flux" or "spider" LED and has four leads instead of two in order to dissipate more heat than the usual 3 mm and 5 mm types. Alternatively, the LED 201 may be a different type.

The LED 201 would typically be attached to a metal bar 203 that serves as a heatsink, conducting heat from the LED. The metal bar 203 is attached to a metal tube 204 that fits inside of the head section of the outer casing 205. The tube 204 serves as additional heatsink means to conduct heat from the LED and to dissipate said heat. Alternatively, if the head section of the outer casing 205 is metal, then the bar 203 may be attached directly to the outer casing. Other heatsinking arrangements may be used. LEDs can be used for this purpose without heatsinking. A narrow circuit board may be attached to or used in place of the metal bar 203.

The reflecting surface 206 of the concave mirror 202 is ideally paraboloidal if the inspection lamp 200 is to be used to illuminate materials at great distances. The reflecting surface 206 of the concave mirror 202 is ideally ellipsoidal if the inspection lamp 200 is to be used for illuminating materials at close distances. Other shapes of the reflecting surface 206 can be found to be usable. Alternatively, a spherical shape for the reflecting surface 206 may be used.

The LED may be placed in a position where the concave mirror 202 forms a beam consisting of an image of the die or "chip" of the LED 201. The LED 201 may be positioned such that the beam formed by the concave mirror 202 consists of an image of another part of the LED such as the edge of a curved portion of the front surface. The LED 201 may be positioned such that no specific part of it is imaged but the beam may be optimized for brightness or sharpness of its edge. It is forseeeable that it may be desirable to place a sheet of opaque material having a hole in it forward of the LED 201 or around the tip of the LED 201 so that the beam consists of an image of the hole and has a sharp edge or other attractive appearance.

A battery 207 provides power for the LED 201. The battery may or may not be rechargeable. Suitable rechargeable battery types include nickel cadmium, nickel metal hydride and lithium ion. The battery may comprise one cell but it is preferred that the battery comprise at least two cells. Circuitry 208 that is typically but not necessarily mounted on a circuit board 209 is typically necessary for the LED 201 to operate. The circuitry 208 may comprise a boost converter, a linear current regulator, a switching current regulator, a resistor, or other circuitry that is found to enable the LED to operate properly from electrical power supplied by the battery 207.

A switch 210 is provided to turn the LED on or off. The switch 210 may be a momentary switch, a non-momentary switch, or a switch that is usable as either a momentary or a non-momentary switch.

If the battery 207 is rechargeable, then a charging connector 211 may be provided so that the battery can be recharged. Alternatively, the battery may be removable. Charging circuitry (not shown) that is used to recharge a rechargeable battery 207 may be but is not necessarily included inside or attached to the inspection lamp 200.

Wires 212a and 212b are typically provided to connect the LED 201 to the circuit board 209. Other wires (not shown) are typically provided to connect the battery 207 to the circuit board 209, the switch 210 and the charging connector 211.

One or more indicator lamps (not shown) may be provided to indicate the status of the battery 207 or for other purposes.

Figure 3:
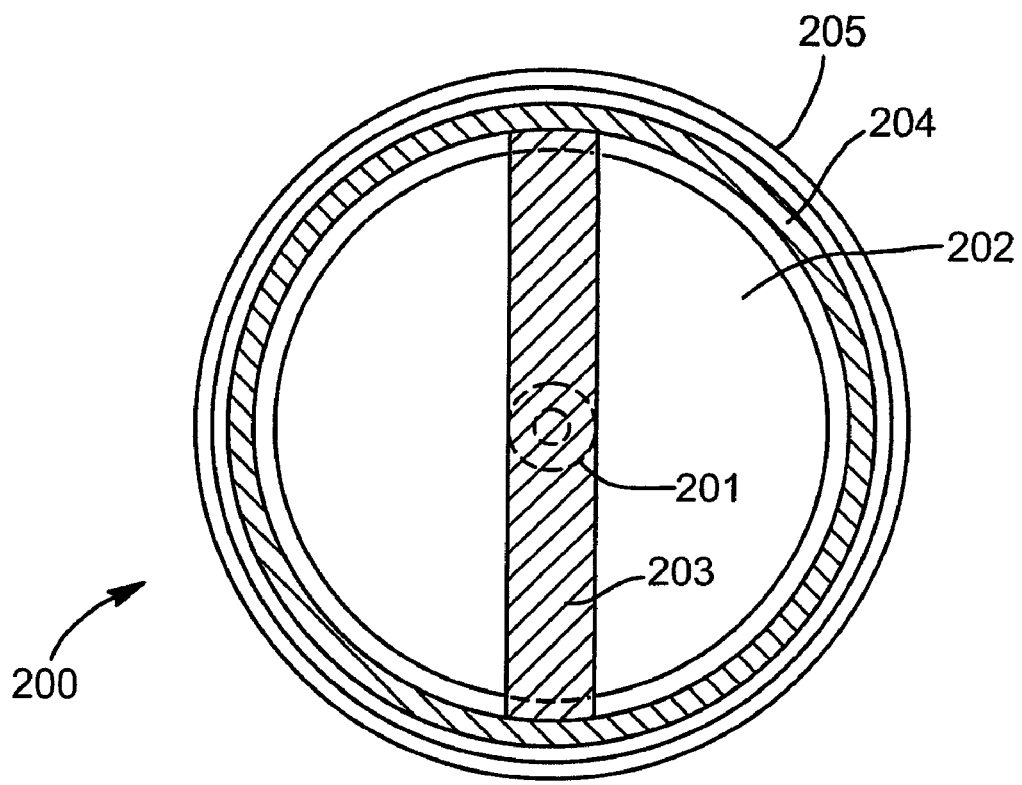
FIG. 3 is a frontal view of said second embodiment of the present invention.

FIG. 3 is a frontal view of the inspection lamp 200 shown in FIG. 2. Shown are the LED 201, the concave mirror 202, the metal bar 203, the metal tube 204 and the outer casing 205.

Figure 4:
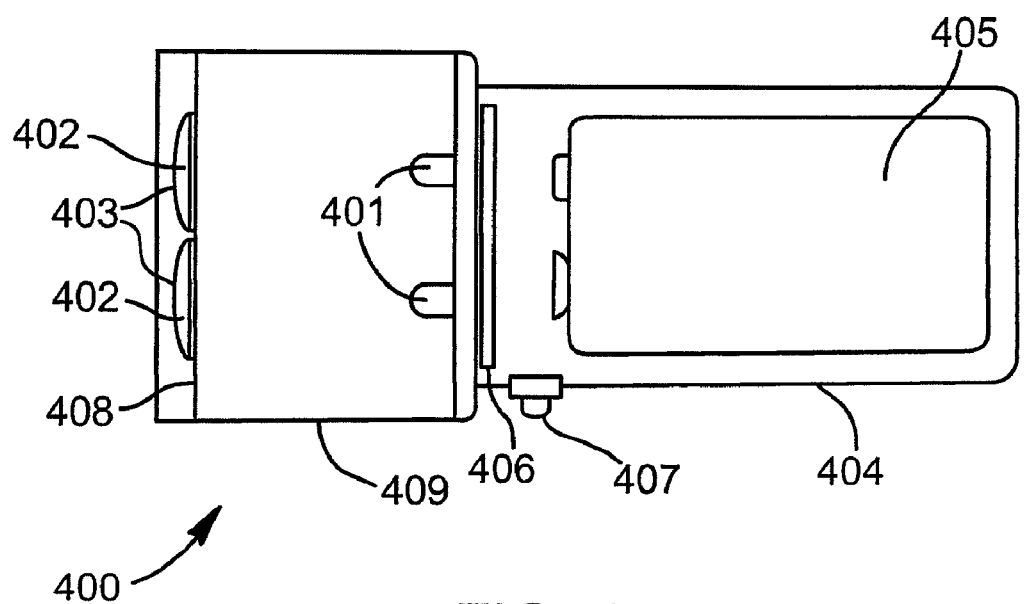
FIG. 4 is a cross sectional side view of a third embodiment of the present invention.

Referring to FIG. 4, a third embodiment of the present invention is an inspection lamp 400 that resembles a flashlight and has lenses 402 to collimate the light from LEDs 401 into beams that merge together into a single beam. The inspection lamp 400 is similar to one described in U.S. Patent Application No. 20020093649, except the curved surfaces 403 of the lenses 401 are not spherical. The text and drawings of U.S. Patent Application No. 20020093649 is hereby incorporated by reference into this detailed description. The curved surfaces 403 may be ellipsoidal. The curved surfaces 403 may have a shape that is a mathematical combination of a paraboloid, an ellipsoid and a sphere. Other aspheric shapes of the curved surfaces 403 of the lenses 402 may be found to be useful. One shape that has been found to be useful is 58% paraboloidal and 42% spherical. This was found suitable if the radius of curvature of the central portions of the curved surfaces is 9.6 millimeters, the overall lens thickness is 4.4 to 5 millimeters, and the refractive index of the lens material is 1.5. This results in an effective focal length of 19.2 millimeters. An equation giving a curve that is 58% paraboloidal and 42% spherical, with a vertex radius of curvature R, is: $y=(0.58*X^2/2R)+(0.42*(R-SQR(R^2-X^2)))$ Although such a lens shape is not quite free of aberrations, it works better than does a lens with a spherical curved surface or a paraboloidal curved surface.

If the curved surfaces 403 are ellipsoidal, then the ellipsoidal surfaces 403 may be a portion of an oblate spheroid that has an aspect ratio of or close to 1.55, since such a shape has been found to work well.

The LEDs 401 may be placed directly rearward of their respective lenses 402, so that the axes of the beams formed thus are parallel to each other and to the central axis of the head section of the inspection lamp 400. Alternatively, each of the LEDs 401 that are not on the axis of the head section of the inspection lamp 400 may be further from said axis than the axes of their corresponding lenses 402 are, so that the beams formed by the lenses 402 converge at a finite distance forward of the lenses 402. The LEDs 401 may be positioned so that the beams consist of images of the chips of the LEDs 401 since doing so typically maximizes the intensity of the beams. The LEDs 401 may be positioned such that the beams consist images of the front surfaces of the LEDs 401, since doing so typically produces attractive beams with sharp edges. The LEDs 401 may be positioned so that no specific parts of them are imaged, although the beams may be optimized for brightness or a particular attractive appearance. It is foreseeable that it may be desirable to place a sheet of opaque material with a hole forward of or around the tip of each of the LEDs 401 so that the beams formed by the lenses consist of images of the holes to give the beams a more attractive appearance such as sharp edges.

The inspection lamp 400 would comprise an outer casing 404, a battery 405, circuitry 406 that is typically necessary for operation of the LEDs 401, a switch 407, and wiring (not shown). The switch 407 may be momentary, non-momentary, or may be able to be used either as a momentary switch or a non-momentary switch.

The LEDs 401 typically have a nominal peak wavelength of 395 to 415 nanometers, although other wavelengths may be found preferable for some applications. The LEDs are typically mounted on an LED board 408.

Figure 5:
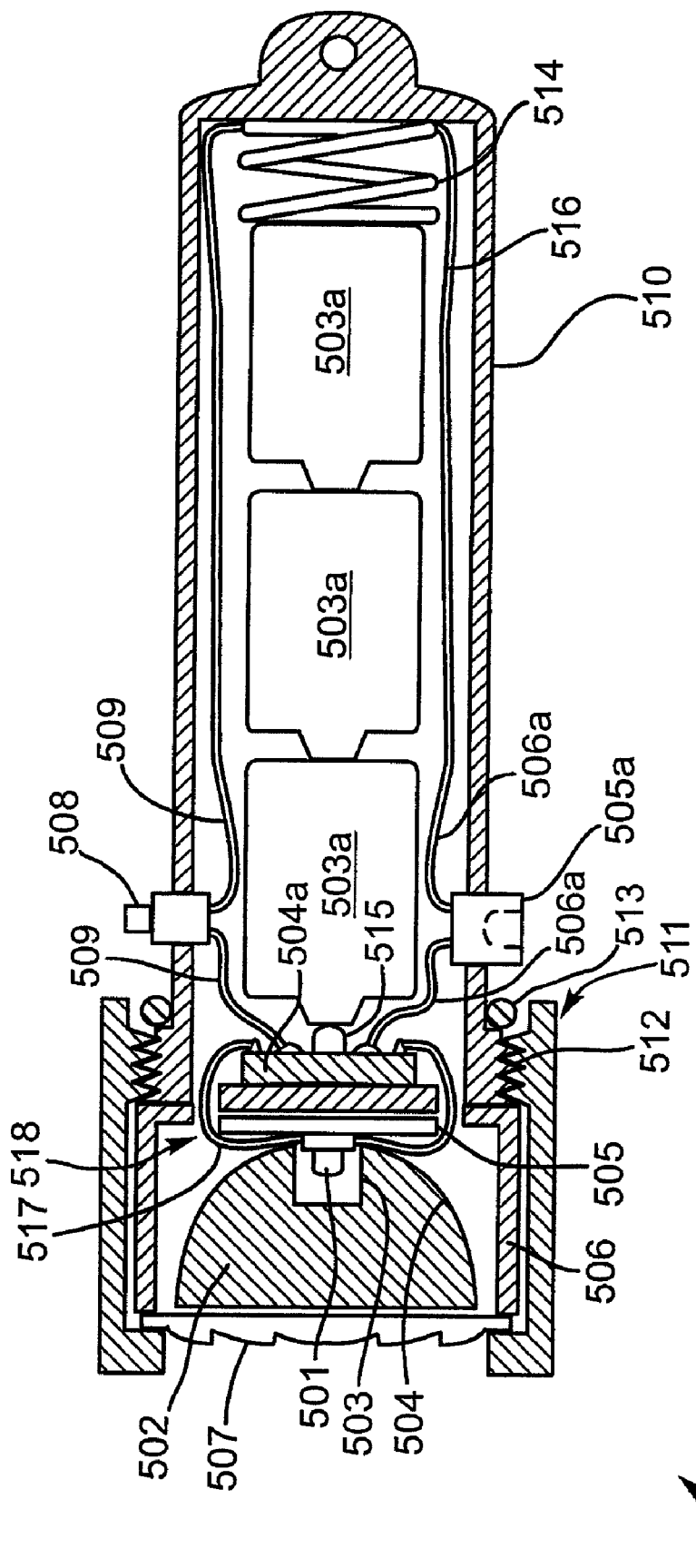
FIG. 5 is a cross sectional side view of a fourth embodiment of the present invention.

The circuitry 406 may be a resistor, a linear current regulator, a switching current regulator, a boost converter, or other circuitry that permits the LEDs 101 to be powered by the battery 405. Preferably the circuit is the switching current regulator of FIG. 4. Alternatively, an alternative switching regulator circuit similar to that of FIG. 5 can be used, since the circuit shown in FIG. 5 is a boost converter that has regulation of the current that flows through a series string of LEDs 401.

The battery may be rechargeable or non-rechargeable. Suitable rechargeable battery types include nickel cadmium, nickel metal hydride, lead-acid, "sealed"/"gel" versions of lead-acid, and lithium ion. If the battery is rechargeable and non-removable, then it will be necessary to provide a charging connector (not shown). A charging circuit (not shown) may be provided in the inspection lamp 400, although in smaller versions of this embodiment of the present invention charging circuitry is typically although not necessarily not provided within the inspection lamp 400.

One or more indicator lamps (not shown) may be provided to indicate the status of the battery 405 or for other purposes.

A flashlight that is intended to produce visible light, whether white or of a color other than white, and having the advantage of aspheric lenses over spherical lenses forward of the LEDs may be achieved by placing appropriate LEDs in place of the fluorescence-causing LEDs 401. The replacement of fluorescence causing LEDs with LEDs for the production of visible light, whether white or of a color other than white, applies equally to all embodiments described herein.

Referring to FIG. 5, a fourth embodiment of the present invention is an inspection lamp 500 that has an LED 501 and a transparent optic 502 that uses reflection or both refraction and reflection to collimate the radiation from the LED 501 into a beam. The transparent optic 502 would typically resemble ones used in the Lumileds "Luxeon with Optics" high power LED light sources, but would typically be larger in order to produce a better beam. The transparent optics used by Lumileds are typically 20 millimeters in diameter, and a transparent optic 502 for the inspection lamp 501 would preferably be 25 to 50 millimeters in diameter.

Much of the radiation from the LED 501 hits the inner surface 503 of a hollow cylindrical region of the transparent optic 502, and as a result is refracted into a direction that is more perpendicular to the axis of the transparent optic 502. After this refraction, the radiation experiences total internal reflection by the rear surface 504 of the transparent optic 502. The total internal reflection directs the radiation forwards. The front surface of the transparent optic 502 may be flat or it may be shaped to refract the radiation as part of collimating the radiation into a beam.

The transparent optic 502 and the LED 501 may be separate parts or they may be combined into a single unit.

The rear surface 504 of the transparent optic 502 may be conical, spherical, paraboloidal, hyperboloidal, ellipsoidal, or of another shape. The rear surface 504 of the transparent optic 502 may comprise zones of different shapes. The front surface of the transparent optic 502 may be planar or curved or comprise zones of different shapes. Any surface of the transparent optic 502 may be faceted. Any surface of the transparent optic 502 may be textured for purposes such as smoothing any irregularities in the beam produced by the transparent optic 502. Advantages of a textured surface of the transparent optic 502 may be realized even if transparent optic 502 is of a typical size of such a part, such as 20 millimeters in diameter.

The transparent optic 502 is typically made of a transparent thermoplastic such as an acrylic. It may be made of a thermoplastic polycarbonate. Alternatively, the transparent optic 502 may be made of a non-thermoplastic polymer such as epoxy, or a non-polymer material such as glass or quartz.

The LED 501 is typically a high power LED that requires heatsinking means. The heatsinking means may comprise a metal disc 505 attached to a metal tube 506, although other arrangements are foreseeable. The disc 505 and tube 506 would typically be made of aluminum, although it is forseeable that other metals such as steel or copper may be used. It is forseeable that any or all of the heatsinking means may be made of diamond should it become economically feasible to make parts of a heatsinking means from diamond.

The LED 501 may be a single chip LED such as a Nichia "1 watt" "Luxeon emitter", an ISP 350 milliamp LED, or an Osram "Golden Dragon" of suitable wavelength. The LED 501 may be a multi chip LED such as a Lumileds "5 watt" "Luxeon Emitter", a Norlux "Hex", or an Opto Electronics model in a TO-66 case. Multi chip LEDs would typically require a larger diameter of the optic 502 to produce an adequately narrow beam. An optic 502 larger in diameter than 50 millimeters may be used with any LED, but is more likely to be necessary if the LED 502 is a multi chip LED with a chip array more than 2 millimeters wide.

The inspection lamp typically further comprises one or more batteries 503a, which may or may not be supplied with the inspection lamp. Any batteries 503a may or may not be rechargeable. Alternatively or additionally, the inspection lamp 500 may be able to receive power from an external power source.

The inspection lamp 500 typically further comprises one or more additional components in a current limiting means 504a that is generally required for reliable stable operation of LEDs such as the LED 501. The current limiting means may be a resistor, a linear current regulator or a switching current regulator. If the LED requires a voltage higher than that supplied by batteries 503a, then the current limiting means 504a may be a boost converter of limited current output. Such a boost converter used as the current limiting means 504a may or may not be a current regulating boost converter.

If any batteries 503a are rechargeable, then they may be recharged through a charging jack 505a. Circuitry that controls recharging may be included in the same circuit board as the current limiting means 504a. The charging jack 505a would be connected to rechargeable batteries 503a or charging circuitry that is included with the current limiting means 504a by means of charging wires 506a.

A lens 507 is typically although not necessarily included to protect internal parts of the inspection lamp 500 from damage by small falling objects, protruding objects, and the like. Typically the front lens 507 would be a planar piece of transparent material, but alternatively the front lens 507 may have optical effects on the radiation emerging from the optic 502. As shown, the lens 507 may be a fresnel lens, although it may be a non-fresnel convex or concave lens.

Typically the inspection lamp 500 would be designed to not require a lens other than a planar lens as the lens 507. However, it may be found desirable for marketing purposes to design an inspection lamp such as the inspection lamp 500 with a deficiency that requires a non-planar lens as the lens 507. For example, a non-planar form of the lens 507 may have an attractive appearance. Attractive front lenses may be used in embodiments of the present invention other than the inspection lamp 500.

An inspection lamp such as the inspection lamp 500 may be of such a design that the front lens 507 may be removed and replaced with a different version of the front lens 507. Changing of the front lens may be desirable for changing the characteristics of the beam of radiation produced by the inspection lamp 500. For example, the beam may be changed from being optimized for longer distances to being optimized for shorter distances.

The front lens 507 may be a filter or a combination of a filter and a non-filtering lens. Such a filter, if used, would typically be a filter that blocks wavelengths longer than the main fluorescence-causing wavelengths produced by the LED 501. Such a filter may be desired if the LED 501 produces some wavelengths that are the same as or similar to wavelengths included in the fluorescence of any fluorescent materials to be detected by use of the inspection lamp 500. Such a filter may be used in other embodiments of the present invention.

The inspection lamp 500 typically further comprises a switch 508, associated switch wiring 509, and an outer casing that may (as shown) comprise a handle casing section 510 and a head casing section 511. Any parts or all of the outer casing may be part of means to heatsink the LED 501. Any parts or all of the outer casing may be made of a metal such as aluminum for heatsinking purposes. Alternatively, any part or all of the outer casing may be made of plastic or another material. As shown, the head casing and handle casing may both have threads 512 so that the head casing section 511 may be screwed onto the handle casing section 510. An o-ring 513 may be provided between separatable parts such as a separate handle section 510 and head section 511 of the outer casing if it is desired to have watertightness of the inspection lamp 500. Other embodiments of the present invention may be watertight models and such other watertight embodiments of the present invention may incorporate o-rings.

Additional parts that the inspection lamp 500 typically includes are battery contacts such as a spring 514 and a non-spring contact 515. Any non-spring contact 515 may be mounted onto the circuit board or assembly that contains the current limiting means 504. The inspection lamp 500 may have one or more battery wires 516 for connecting to the batteries 503 or any of the battery contacts 514 and/or 515. The inspection lamp 500 may have wires connecting to the LED 501. The wires 517 may pass through holes 518 in the heatsink disc 505 or through other parts of any heatsinking means. Where any wires 517 pass through any holes 518, glue or moldable plastic or rubber or other material may be added for reasons such as achieving watertightness of any portion or part of the inspection lamp 500 or reducing any fatigue-causing movement of such wires 517.

The LED 501 may produce radiation whose spectum is a narrow band peaking at 450 nm, since such a wavelength causes fluorescence of some body fluids but not of fabric fibers that have fluorescent optical brighteners added to them. The LED 501 may have a peak wavelength in the 395–415 nanometer range, which is known to be useful for causing fluorescence of leaks of suitably dyed lubricants associated with refrigerants in air conditioning systems and other refrigeration systems. Although other wavelengths are also known suitable for detection of refrigerant leaks, the 395–415 nanometer range is desirable for being visible enough to see what area is being illuminated with the radiation from the LED 501, but not so visible as to excessively interfere with seeing of fluorescent dye that has leaked. Wavelengths longer than 415 nanometers typically require yellow viewing glasses that block most of the radiation produced by the LED 501. Wavelengths slightly shorter than 395 nanometers may be found adequately visible for seeing the area being illuminated with radiation from the LED 501, and it is forseeable that peak wavelengths as short as 380 nanometers or even shorter may be associated with adequate visibility of at least some of the radiation in the main spectral band produced by the LED 501. LEDs with even shorter peak wavelengths such as 365 nanometers may be adequately visible, due to either or both of a "long wavelength tail" of the main ultraviolet emission band of the LED 501, or a secondary longer wavelength emission band produced by LED 501. Ultraviolet LEDs often produce a secondary emission band that peaks in the yellow at a wavelength not far from 575 nanometers. The LED 501 may be an ultraviolet LED that includes or has added to it fluorescent material that produces a small amount of visible light. In any version of the LED 501 that has fluorescent material added, the purpose of the fluorescent material may be to give some visibility to the radiation produced by the LED 501. Alternatively, in any version of the LED 501 that has fluorescent material added, the original purpose may be different and the visible fluorescence may be a side effect. For example, the LED 501 may have an epoxy body made with an epoxy that has an ultraviolet stabilizing agent that is slightly fluorescent.

The LED 501 may produce radiation of any wavelength that is suitable for any application of an inspection lamp. At least two different automotive radiator coolant dyes are excited well by wavelengths in or near the range of 460 to 505 nanometers. Rhodamine 6G, which is used in some forensic work, is excited best by wavelengths near 530 nanometers. An inspection lamp that produces visible red wavelengths but not infrared may be found useful for finding traces of chlorophyll, although such an application requires viewing means sensitive to the near-infrared fluorescence that chlorophyll has but not sensitive to the visible red wavelengths used to cause fluorescence of chlorophyll. The viewing means may be a camera with a suitable filter. Such a camera may be a film camera, digital camera, or a camera using a vacuum imaging tube. If the camera is not a film camera, then the camera or system using such a camera may work in real time or may not do so. Any cameras used for viewing areas illuminated by one or more inspection lamps may be still cameras or movie cameras.

Figure 6:
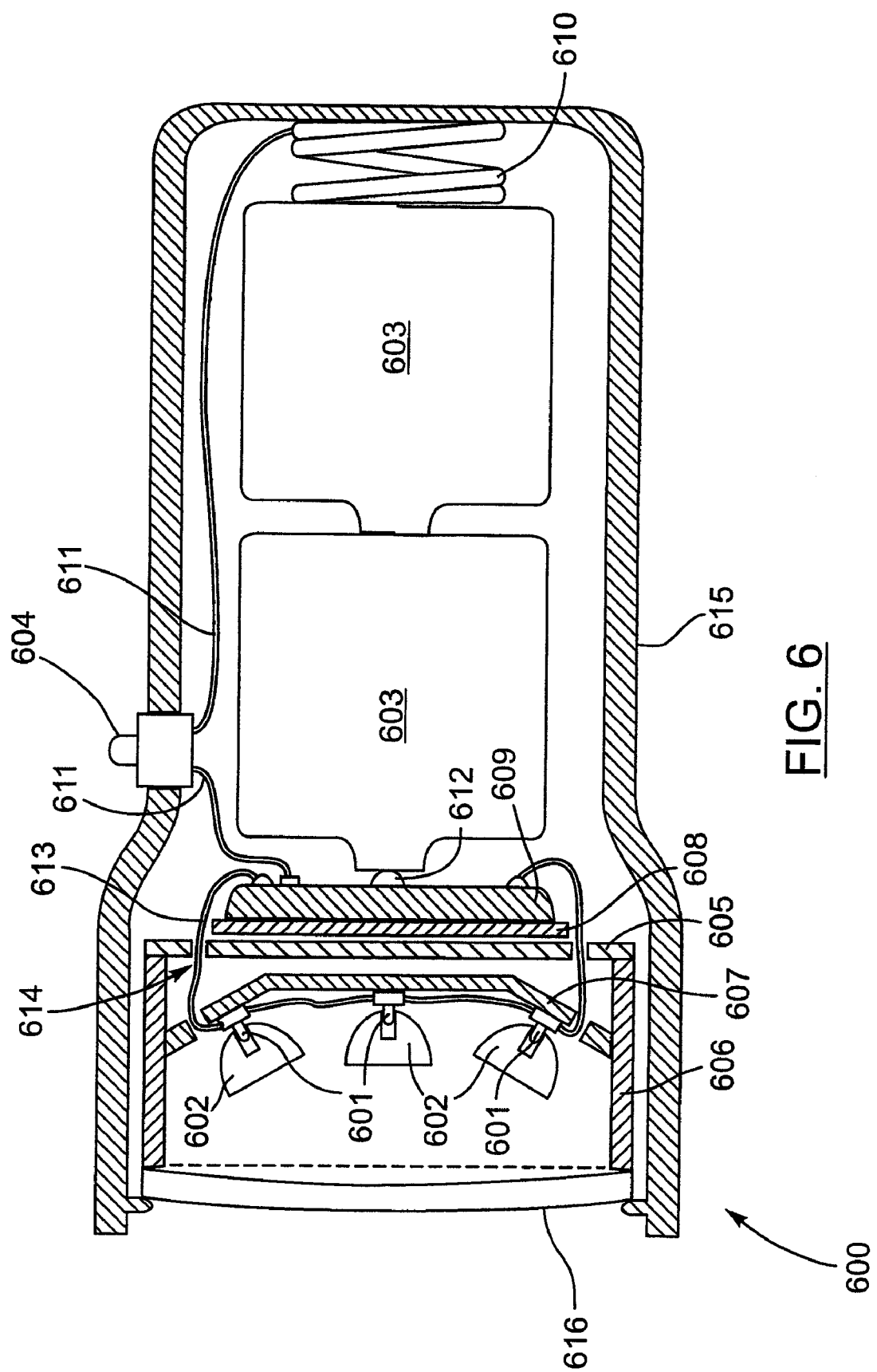
FIG. 6 is a cross sectional side view of a fifth embodiment of the present invention.

Referring to FIG. 6, a fifth embodiment of the present invention is an inspection lamp 600 that has more than one LED 601, each associated with a transparent optic 602 that relies on total internal reflection for collimating the radiation from each of the LEDs 601 into a beam.

As shown, the LEDs 601 and their associated optics 602 may be arranged so that their beams converge at a finite distance or "target distance" forward of the inspection lamp 600. Alternatively, the beams formed from each of the LEDs 601 by their associated optics 602 may be aimed directly forward so as to converge at infinite distance and to be essentially converged at far but finite distances.

The main difference between the inspection lamp 600 shown in FIG. 6 and the inspection lamp 500 shown in FIG. 5 is that the inspection lamp 600 shown in FIG. 6 has more than one LED 601 with an associated optic transparent 602 that uses total internal reflection.

Any rear surfaces 604 of the transparent optics 602 may be conical, spherical, paraboloidal, hyperboloidal, ellipsoidal, or of another shape. Any rear surfaces 604 of the transparent optics 602may or may not comprise zones of different shapes. Any front surfaces of the transparent optics 602 may be planar or curved or comprise zones of different shapes. Any surface of any of the transparent optics 602 may be faceted. Any surface of any of the transparent optics 602 may or may not be textured for purposes such as smoothing any irregularities in the beam produced by the transparent optic 602. Advantages of a textured surface of any of the transparent optics 602 may be realized even if transparent optics 602 are of a typical size of such parts, such as 20 millimeters in diameter.

The transparent optics 602 are typically made of a transparent thermoplastic such as an acrylic. It may be made of a thermoplastic polycarbonate. Alternatively, the transparent optics 602 may be made of a non-thermoplastic polymer such as epoxy, or a non-polymer material such as glass or quartz. The transparent optics 602 may be identical or non-identical in material, shape, and/or size.

Any of the LEDs 601 may or may not have their associated transparent optics 602 combined with them to make LEDs 601 which the transparent optics 602 are an integral part of.

The inspection lamp 600 is shown with one or more batteries 603. Any batteries 603 may or may not be rechargeable. Alternatively, any embodiment of the present invention shown or implemented with batteries can be made in a version that uses an external power supply. Such an external power supply may be one or more external batteries such as an automotive battery. Alternatively, any external power supply may be a non-battery type such as a "wall wart" power supply.

The inspection lamp 600 is shown with a switch 604. In any embodiment of the present invention, such a switch may be momentary, a non-momentary type such as push-on/push-off, or a type that can be used both as a non-momentary switch and as a momentary switch. For example, the switch 604 may be a switch that is of a "push-on/push-off" type that can be usable as a momentary switch if pushed only partway down after being "off". Alternatively, a switch that can be temporarily turned "off" by being partially depressed could be used in alternative embodiments of the present invention.

The inspection lamp 600 is shown with LED heatsinking means comprising a typically metal plate 605 and a typically metal tube 606 that is attached to the plate 605. The inspection lamp 600 is shown including an additional non-flat heatsinking plate 607 which may be desirable in inspection lamps that have heatsinkable LEDs whose optical axes are not parallel with each other. Other embodiments of the present invention may incorporate similar or other LED heatsinking means.

The inspection lamp 600 is shown with a circuit board 608 and associated circuitry 609. The circuitry 609 may be one or more resistors or other current limiting means that the LEDs 601 typically require. The circuitry 609 may be a boost converter, which may be used if any or any combination of the LEDs 601 have a voltage drop in excess of the voltage provided by any batteries 603 or provided by any external power supply (not shown). If the circuitry 609 comprises a boost converter, the boost converter may be a current-regulating boost converter.

The circuitry 609 may include additional circuitry such as battery charging control circuitry or circuitry used for indicating any status of battery condition or battery charging or other electronically discernable conditions of the inspection lamp 600. Any circuitry that could be used in the inspection lamp 600 may be used in other embodiments of the present invention.

The inspection lamp 600 may include a battery contact spring 610 and typically includes switch wiring 611. As shown, one of the wires in the switch wiring 611 may connect the switch to the negative connection of any batteries 603 or of whatever source of power is being used. Alternatively, a wire in the switch wiring 611 that connects the switch to the power supply may be connected to the positive connection of the power supply.

As shown, the circuit board 608 may have a battery contact 612 to make contact with the positive terminal of one of one of any batteries 603. Alternatively, such a circuit board battery contact 612 may be intended to contact the negative terminal of one of any batteries 603. Further alternatively, such a battery contact 612 may be located somewhere other than on the circuit board 608 and this may require adding a wire (not shown) to connect the circuit board 608 to the battery contact 612.

Wires 613 may be connected to the LEDs 601. Any wires 613 may pass through holes 614 in any parts of any heatsinking means such as the shown heatsinking plates 605, 607. Any holes such as holes 614 that any wires such as wires 613 pass through may be filled with sealing material or material that reduces possibly damaging movement of such wires.

The inspection lamp is shown with a single piece outer casing 615. Alternatively, embodiments of the present invention can have multiple piece outer casings. Part or all of the outer casing 615 may be part of means to heatsink the LEDs 601. The outer casing 615 may be made of aluminum or another metal for heatsinking purposes. Alternatively, part or all of the outer casing 615 may be made of plastic or another material.

The inspection lamp 600 includes a front lens 616 that may be a planar piece of transparent material. The front lens 616 of the inspection lamp 600 or any front lens of alternative embodiments of the present invention may be glass, quartz, thermoplastic or non-thermoplastic polymer material. The front lens 616 or any front lens of alternative embodiments of the present invention may have filtering characteristics, such as passing fluorescence-causing wavelengths of the radiation produced by the LEDs 601 while blocking wavelengths of radiation produced by the LEDs 601 but also produced by fluorescent materials being detected by such an inspection lamp.

Figure 7:
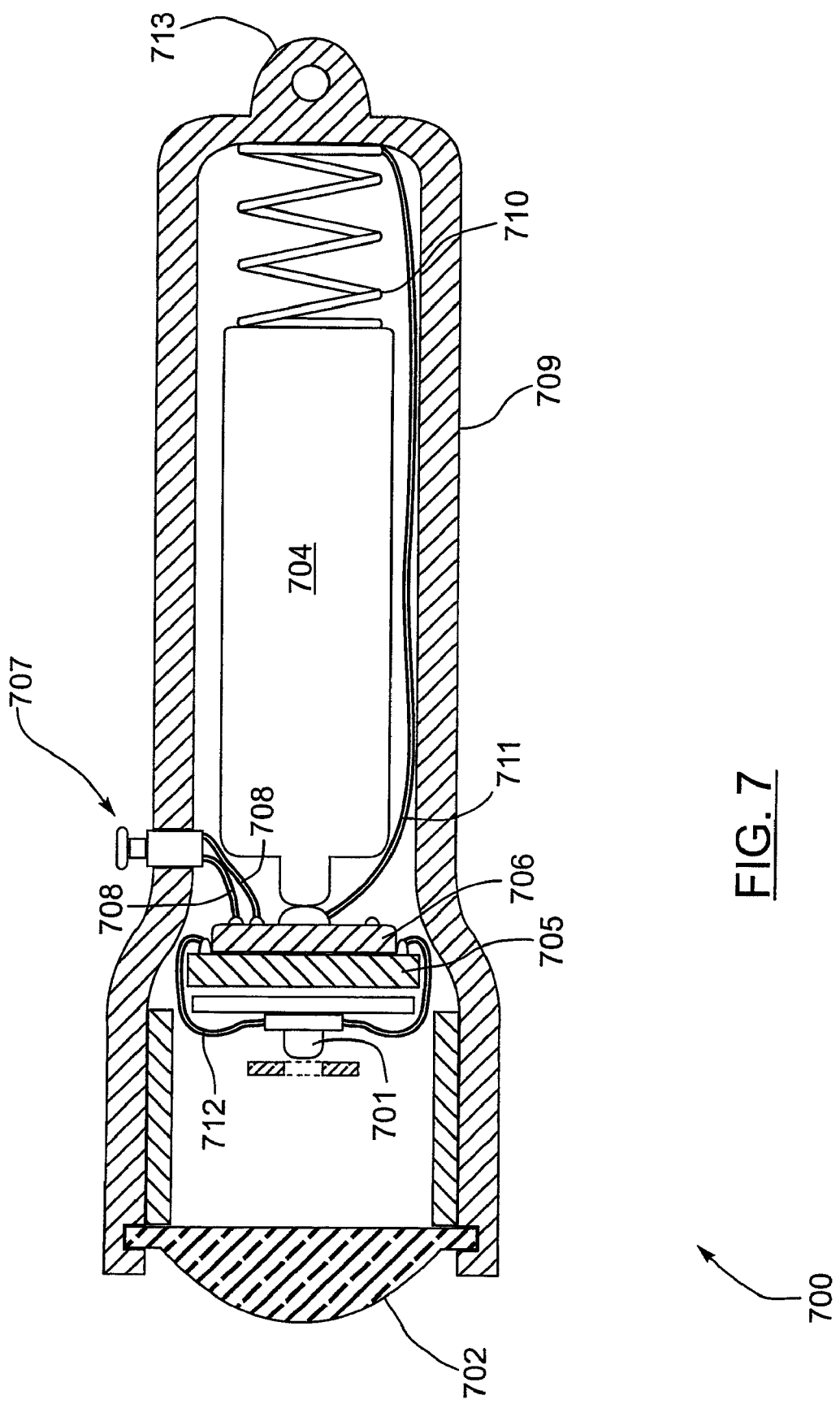
FIG. 7 is a cross sectional side view of a sixth embodiment of the present invention.

Referring to FIG. 7, a sixth embodiment of the present invention is an inspection lamp 700 that comprises a single LED 701 and an aspheric lens 702 that collimates the radiation from the LED 701 into a beam. The aspheric lens provides a more sharply focused beam than a lens having only one or more spherical surfaces can.

The aspheric lens 702 may be planoconvex as shown, but alternatively may be biconvex or concavoconvex. If the lens 702 has both its front and rear surfaces curved, then either or both of these surfaces may have an aspheric curvature. Such an aspheric curvature may be paraboloidal, ellipsoidal, hyperboloidal or any combination of these or any combination of any of these and spherical curvature. For example, a lens with a focal length of 35 millimeters may have a curve that deviates from a flat surface by the sum, in terms of deviating from a plane, of a spherical surface that alone results in a focal length of 70 millimeters and a paraboloidal surface that alone results in a focal length of 70 millimeters.

The aspheric lens 702 may be in a fresnel lens form. If the lens 702 has more than one non-planar surface, either or both surfaces may be fresnel lens surfaces.

The inspection lamp 700 may have a washer (annular ring) 703 that is placed at or near the most forward point of the LED 701. The beam produced by the inspection lamp 700 may be in the form of an image of the hole of the washer 703. Alternatively, the beam produced by the inspection lamp 700 may be in the form of an image of a hole or transparent region in an object other than the washer 703 or of the edge of the transparent body of the LED 701 or of the chip or chip array of the LED 701 or of any other part of the LED 701. Further alternatively, the beam produced by the inspection lamp 700 may not be in the form of a focused image of any part of the inspection lamp 700.

The inspection lamp 700 as shown further comprises a battery 704, a circuit board 705, circuitry 706 that the LED 701 typically requires, a switch 707, switch wiring 708, an outer casing 709, a battery spring contact 710, one or more battery wires 711, and a closed loop formation 713 that is provided for attachment of a lanyard. Other arrangements are forseeable for an inspection lamp that has a single LED and an aspheric lens that collimates the radiation from the LED into a beam.

Figure 8:
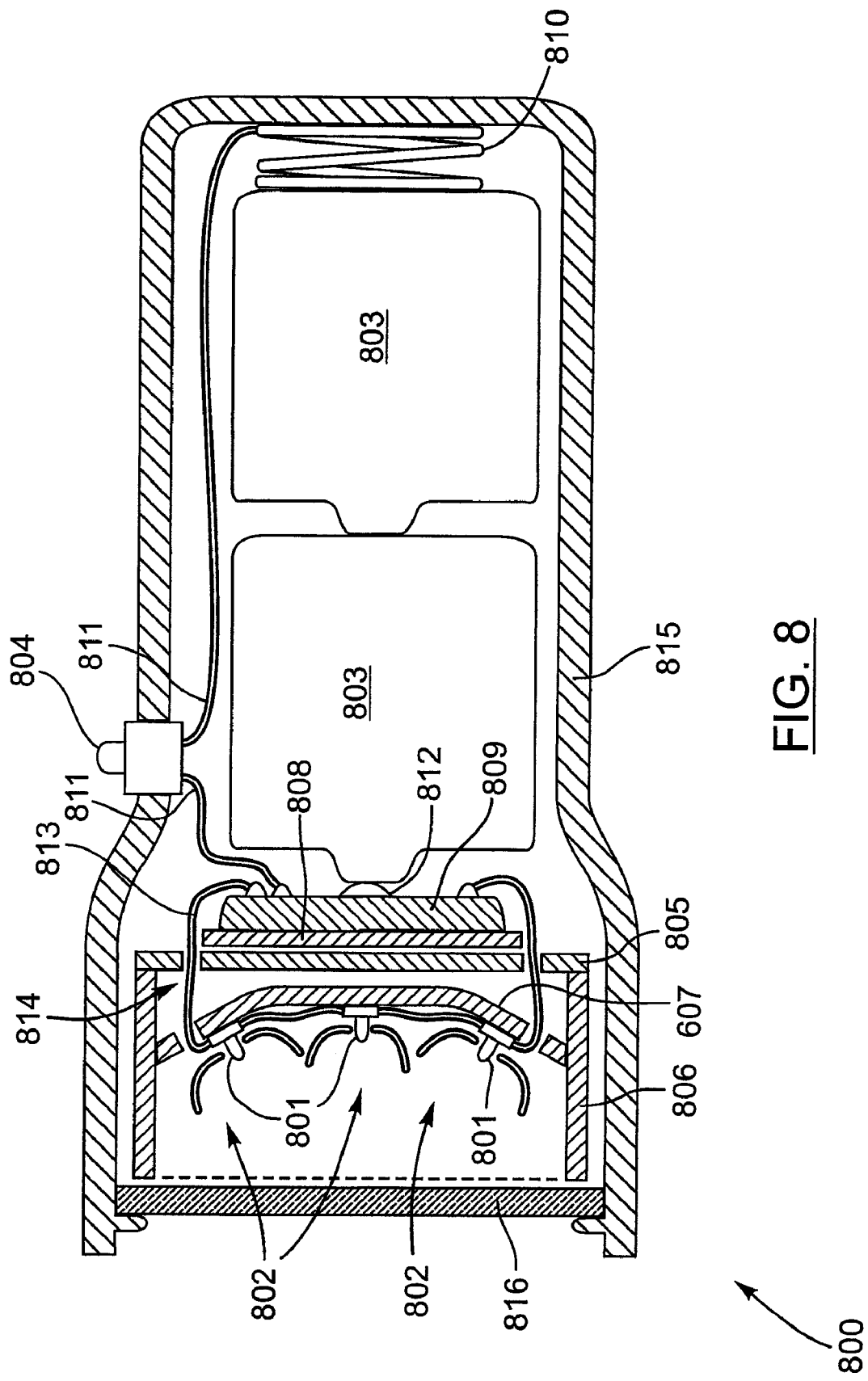
FIG. 8 is a cross sectional side view of a seventh embodiment of the present invention.

Referring to FIG. 8, a seventh embodiment of the present invention is an inspection lamp comprising two or more LEDs 801 that are pointed generally forwards, with each of the LEDs 801 associated with a concave mirror 802 to collimate the radiation produced by the LEDs 801 into a beam. The concave mirrors 802 may be separate pieces or comprised into a single piece. The concave mirrors 802 may be metal, metallized glass or metallized plastic.

The concave mirrors 802 may or may not have a protective overcoating. If any concave mirrors 802 have a protective overcoating, the protective overcoating may be silicon dioxide. Any protective overcoating on any concave mirrors 802 may be a polymer. Any protective overcoating on any concave mirrors 802 may be sprayed on or applied in a manner other than spraying, such as being applied with a paintbrush or similar means. Any protective coating may or may not require curing or solidification such as by evaporation of a solvent, inherent reaction of chemical ingredients in the protective coating, or oxidation or polymerization. Curing of any protective coating on any mirrors 802 may or may not require or be assisted by irradation by ultraviolet radiation or other radiation. Any concave mirrors 802 may or may not require elevated temperatures in their formation, such as for curing of any protective coating.

The LEDs 801 may be identical or they may be non-identical. It is preferred that at least one of the LEDs 801 produce visible light to an extent such that the area being illuminated with the inspection lamp is visible being illuminated. Any of the LEDs 801 that produces such visible radiation would preferably produce radiation, whether visible or in the form of additional invisible radiation, that is suitable for causing fluorescence of fluorescent materials to be detected by use of the inspection lamp 800. It is preferred that all of the LEDs 801 produce radiation that is suitable for causing fluorescence of materials to be detected, although foreseeable alternative embodiments of the present invention can have some but not all of the LEDs 801 producing radiation that is useless for causing fluorescence of at least some fluorescent materials.

The concave surfaces of the mirrors 802 may be spherical or aspheric. Aspheric concave surfaces of the mirrors 802 would ideally be paraboloidal for forming beams that are best-formed at infinite and long distances, while ellipsoidal concave surfaces of the mirrors 802 would be ideal if the inspection lamp 800 is to be optimized for shorter distances. Any of the concave mirrors 802 may be faceted or textured.

The concave mirrors 802 and LEDs 801 may be arranged to form beams that merge best at infinite distance and nearly enough do so at far but finite distances. Such an arrangement that is optimized for long distances may be found adequate for use at shorter distances of a meter or a fraction of a meter forward of the inspection lamp 800. Alternatively, the concave mirrors 802 and LEDs 801 may be arranged to form beams that are best-merged and best-focused at a finite distance forward of the inspection lamp 800. Preferably the distance at which the beams are best focused would be the same distance that the beams are best merged into each other, although it is foreseeable that at a finite distance forward of the inspection lamp the beams may be best-focused or best-merged but not both. It is foreseeable that a variation of the inspection lamp 800 or another embodiment of the present invention with multiple beams may have its beams either not converge or not focus at any finite distance, although it is preferred that the beams are both reasonably well defined and reasonably merged into each other at a target distance forward of such an inspection lamp that such an inspection lamp would be used for.

The inspection lamp 800 typically further comprises a lens 816. The lens 816 is typically but not necessarily a planar piece of transparent material, such as by example and not limitation glass, quartz, acrylic, thermoplastic polycarbonate, non-thermoplastic polycarbonate, or epoxy. The lens 816 may have filtering properties, such as blockage of wavelengths produced both by any or all of the LEDs 801 and at least some of the fluorescent materials that the inspection lamp 801 is intended to cause fluorescence of.

The lens 816 may have refractive properties not achieved by the concave mirrors 802. A foreseeable purpose of a design of the inspection lamp 800 wherein the concave mirrors 802 produce beams requiring refractive action of the lens 816 is to accomodate a version of the lens 816 that has a marketable appearance of having a part in formation of the beams of radiation that are at least partially formed by the concave mirrors 802. It may be found that the concave mirrors 802 could be found to be made smaller or less expensive to produce if the lens 816 plays a role in the formation of beams of radiation partially formed by the concave mirrors 802 from the LEDs 801.

The inspection lamp 800 is shown with one or more batteries 803. Any batteries 803 may or may not be rechargeable. Alternatively, any embodiment of the present invention shown or implemented with batteries can be made in a version that uses an external power supply. Such an external power supply may be one or more external batteries such as an automotive battery. Alternatively, any external power supply may be a non-battery type such as a "wall wart" power supply.

The inspection lamp 800 is shown with a switch 804. In any embodiment of the present invention, such a switch may be momentary, a non-momentary type such as push-on/push-off, or a type that can be used both as a non-momentary switch and as a momentary switch. For example, the switch 804 may be a switch that is of a "push-on/push-off" type that can be usable as a momentary switch if pushed only partway down after being "off". Alternatively, a switch that can be temporarily turned "off" by being partially depressed could be used in alternative embodiments of the present invention.

The inspection lamp 800 is shown with LED heatsinking means comprising a typically metal plate 805 and a typically metal tube 806 that is attached to the plate 805. The inspection lamp 800 is shown including an additional non-flat heatsinking plate 807 which may be desirable in inspection lamps that have heatsinkable LEDs whose optical axes are not parallel with each other. Other embodiments of the present invention may incorporate similar or other LED heatsinking means.

The inspection lamp 800 is shown with a circuit board 808 and associated circuitry 809. The circuitry 809 may be one or more resistors or other current limiting means that the LEDs 801 typically require. The circuitry 809 may be a boost converter, which may be used if any or any combination of the LEDs 801 have a voltage drop in excess of the voltage provided by any batteries 803 or provided by any external power supply (not shown). If the circuitry 809 comprises a boost converter, the boost converter may be a current-regulating boost converter.

The circuitry 809 may include additional circuitry such as battery charging control circuitry or circuitry used for indicating any status of battery condition or battery charging or other electronically discernable conditions of the inspection lamp 800. Any circuitry that could be used in the inspection lamp 800 may be used in other embodiments of the present invention.

The inspection lamp 800 may include a battery contact spring 810 and typically includes switch wiring 811. As shown, one of the wires in the switch wiring 811 may connect the switch to the negative connection of any batteries 803 or of whatever source of power is being used. Alternatively, a wire in the switch wiring 811 that connects the switch to the power supply may be connected to the positive connection of the power supply.

As shown, the circuit board 808 may have a battery contact 812 to make contact with the positive terminal of one of one of any batteries 803. Alternatively, such a circuit board battery contact 812 may be intended to contact the negative terminal of one of any batteries 803. Further alternatively, such a battery contact 812 may be located somewhere other than on the circuit board 808 and this may require adding a wire (not shown) to connect the circuit board 808 to the battery contact 812.

Wires 813 may be connected to the LEDs 801. Any wires 813 may pass through holes 814 in any parts of any heatsinking means such as the shown heatsinking plates 805, 807. Any holes such as any holes 814 that any wires such as any wires 813 pass through may be filled with sealing material or material that reduces any possibly damaging movement of such wires.

The inspection lamp is shown with a single piece outer casing 815. Alternatively, embodiments of the present invention can have multiple piece outer casings. Part or all of the outer casing 815 may be part of means to heatsink the LEDs 801. The outer casing 815 may be made of aluminum or another metal for heatsinking purposes. Alternatively, part or all of the outer casing 815 may be made of plastic or another material.

The inspection lamp 800 includes a front lens 816 that may be a planar piece of transparent material. The front lens 816 of the inspection lamp 800 or any front lens of alternative embodiments of the present invention may be glass, quartz, thermoplastic or non-thermoplastic polymer material. The front lens 816 or any front lens of alternative embodiments of the present invention may have filtering characteristics, such as passing fluorescence-causing wavelengths of the radiation produced by the LEDs 801 while blocking wavelengths of radiation produced by the LEDs 801 but also produced by fluorescent materials being detected by such an inspection lamp.

Figure 9:
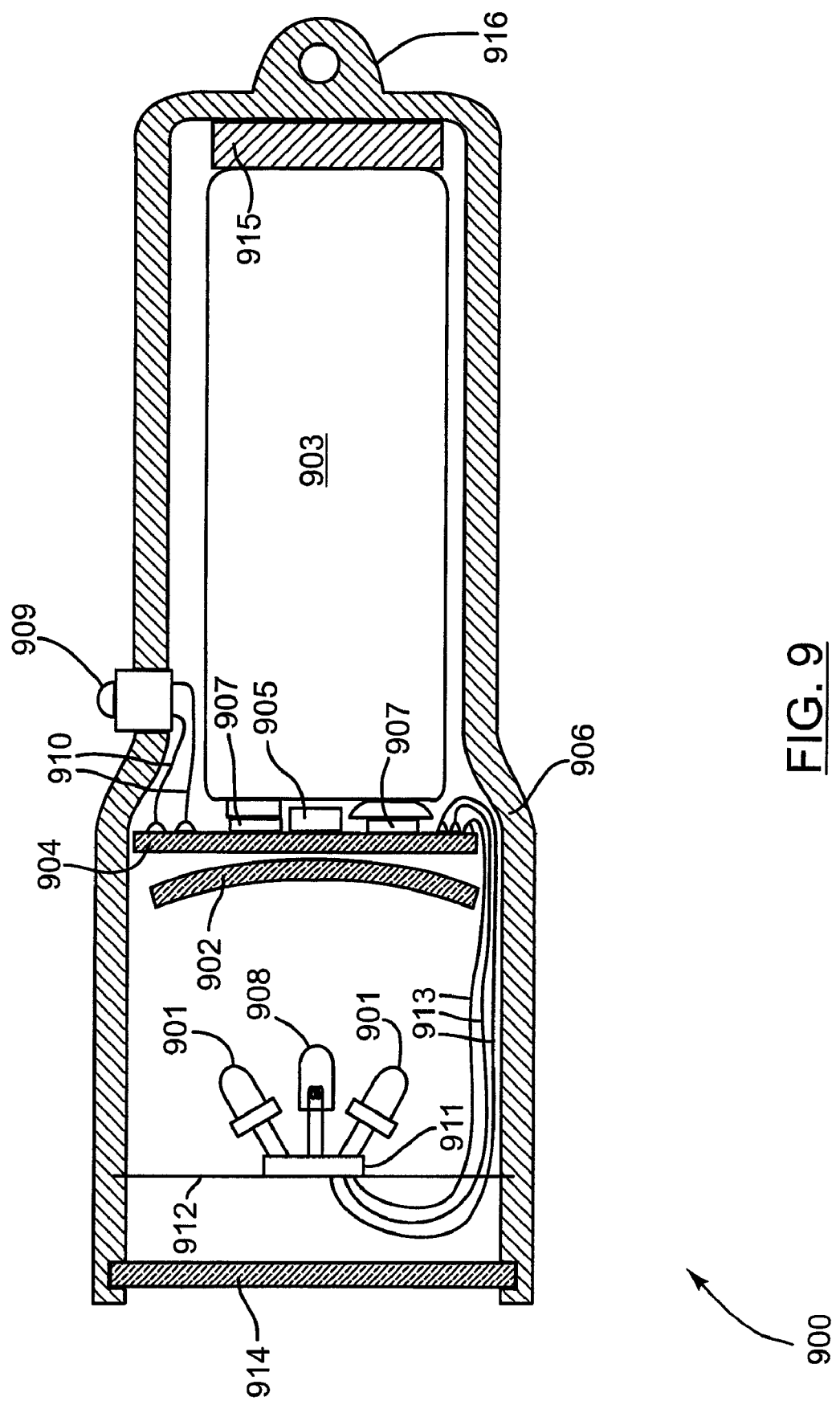
FIG. 9 is a cross sectional side view of an eighth embodiment of the present invention.

Referring to FIG. 9, an eighth embodiment of the present invention may be an inspection lamp 900 that comprises a small cluster of LEDs 901 that are aimed rearwards towards a single concave mirror 902. If the inspection lamp is of a design optimized for infinite distances or longer distances of a meter or more, then ideally the concave mirror 902 is paraboloidal and the LED axes are colinear with lines that both pass through the focal point of the concave mirror 902 and points on the surface of the concave mirror 902. If the inspection lamp 900 is of a design optimized for shorter target distances, then the concave mirror 902 may be ellipsoidal with two focal points, a distal focal point at the designed target distance and a proximal focal point which the axes of the LEDs 901 ideally pass through. It is foreseeable that alternative designs can be found to be workable. Such an alternative design may include the concave mirror 902 having a spherical reflective surface.

The concave mirror 902 may or may not comprise a plurality of facets. The concave mirror 902 may or may not be textured. If the concave mirror 902 is textured, this may be done to smooth out irregularities in the beam formed by it or to achieve an attractive appearance.

The concave mirror 902 may or may not have a protective overcoating. If any concave mirror 902 have a protective overcoating, the protective overcoating may be silicon dioxide. Any protective overcoating on any concave mirror elements 902 may be a polymer. Any protective overcoating on any concave mirror 902 may be sprayed on or applied in a manner other than spraying, such as being applied with a paintbrush or similar means. Any protective coating may or may not require curing or solidification such as by evaporation of a solvent, inherent reaction of chemical ingredients in the protective coating, or oxidation or polymerization. Curing of any protective coating on any mirror 902 may or may not require or be assisted by irradation by ultraviolet radiation or other radiation. The mirror 902 may or may not require elevated temperatures in their formation, such as for curing of any protective coating.

The inspection lamp 900 typically further comprises a battery 903, although the inspection lamp 900 may alternatively receive power from an external battery or other external power source.

The battery 903 may have both its positive and negative terminals on one end, as shown. The inspection lamp typically further comprises a circuit board 904. Such a circuit board 904 typically has mounted on it current limiting means 905 that the LEDs 901 typically require. The current limiting means 905 may comprise one or more resistors, one or more linear current regulators, one or more switching current regulators, and/or one or more boost converters that have limited current output. Any of one or more boost converters used in the current limiting means 905 may have regulated current output.

The inspection lamp 900 typically further comprises an outer casing 906, which is shown as being of a single piece of material. The outer casing 906 may alternatively consist of more than one piece. If the outer casing 906 comprises more than one piece of material, then such multiple pieces of the outer casing may or may not be made of the same material. For example, part of the outer casing 906 may be made of metal and part of the outer casing 906 may be made of a plastic such as ABS, acrylic, thermoplastic polycarbonate, polyethylene, polypropylene, polybutylene or "nylon".

Since the inspection lamp 900 is shown as having a battery 903 having both its positive and negative terminals at the same end of the battery 903, the circuit board 904 can include the typically required battery contacts 907.

In the inspection lamp 900, the LEDs 901 may but not necessarily produce essentially invisible ultraviolet radiation. It is often desirable for inspection lamps such as the inspection lamp 900 to produce a beam that is sufficiently visible to slightly visibly illuminate the area that is being irradiated by inspection lamps such as the inspection lamp 900. Therefore, the inspection lamp 900 may further comprise a visible light source 908 which may be an incandescent lamp (as shown) or which may be an LED.

The inspection lamp 900 typically further comprises a switch 900. The switch 900 may be of a non-momentary type, a momentary type, or a type usable both as a momentary and as a non-momentary switch. The switch 909 typically has connected to it switch wires 910. As shown, the switch wires 910 may run to the circuit board 904, but alternatively at least one of the switch wires 910 may run to a connector for the battery 903 or to the LEDs 901.

The LEDs 901 may be mounted to an LED board 911. Such an LED board 911 may be held in place by thin rods 912 (as shown).

As shown, the LED board 911 may be connected to the circuit board 904 by means of wires 913.

The inspection lamp 900 typically includes a front lens 914. The front lens 914 may have filtering characteristics such as blocking of wavelengths both produced by the LEDs 901 and by materials that the inspection lamp 900 is intended to cause fluorescence of. The front lens 914 is typically planar but may not be. The concave mirror 902 may be located or of such curvature that the beam formed by it can be improved by making the front lens 914 convex or concave. If the font lens 914 is convex or concave, it may be spherical or aspheric. An aspheric version of the front lens 914 may be ellipsoidal, paraboloidal, hyperboloidal, a curve that is any mathematical combination of such shapes with each other or other shapes, or it may be of another curved shape. A convex version of the front lens may be biconvex, planoconvex, concavoconvex or a fresnel lens. A concave version of the front lens 914 may be biconcave, planoconcave, convexoconcave, or a fresnel lens. The front lens may be translucent, frosted or textured if a diffusing characteristic is desirable for purposes such as smoothing irregularities in the beam formed by the concave mirror 902.

The LED board 911 may be attached to the front lens 914.

In an inspection lamp having a battery that has both terminals on one end, such as the inspection lamp 900 having a battery resembling the shown battery 903, a piece of foam rubber 915 may be provided to keep the battery forced into a desirable position. Other arrangements are foreseeable where one or more pieces of foam rubber are desirable to keep any batteries or other parts forced into a desirable position.

The inspection lamp 900 may but does not necessarily further comprise a closed loop formation 916 that is suitable for attachment of a lanyard.

Figure 10:
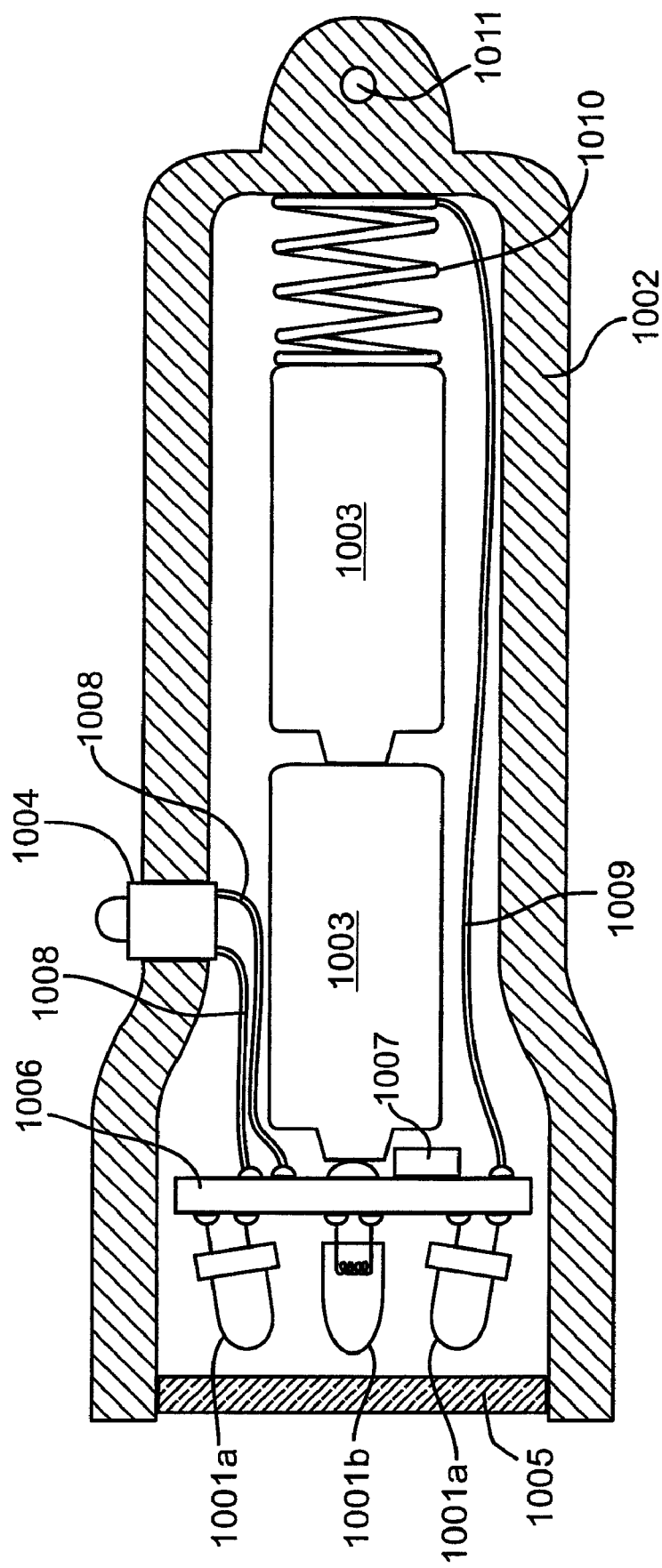
FIG. 10 is a cross sectional side view of a ninth embodiment of the present invention.

Referring to FIG. 10, a ninth embodiment of the present invention is an inspection lamp 1000 that has one or more LEDs 1001a that produce invisible or essentially invisible ultraviolet radiation, and at least one light source 1001b that produces radiation that is more visible. The one or more visible-radiation-producing light sources 1001b may be LEDs or non-LED lamps such as incandescent lamps. It is preferred that the radiation from the visible-radiation-producing light source(s) 1001b be useful for causing fluorescence of fluorescent materials to be detected with the inspection lamp 1000. The visible radiation produced by the one or more visible-radiation-producing lamps 1001b would typically be used for forming a visible beam that is usually desirable for indicating the area that is being illuminated by an inspection lamp such as the inspection lamp 1000. This is an alternative to inspection lamps that have a single light source or more than one identical light sources that produce radiation that both has a desirable visibility and ability to cause fluorescence of fluorescent materials.

The visible-radiation-producing light source shown in FIG. 10 is a filament lamp, but it may be an LED or other light source such as a glow discharge lamp, arc lamp, or electroluminescent lamp. More than one visible light source may be used as the one or more visible light sources 1001b. If any of the one or more visible light sources 1001b is an LED, it may be a less-conventional LED such as a laser diode, an organic LED, or polymer LED. If any of the one or more visible light sources is a semiconducter LED, the LED chemistry may be but is not necessarily limited to GaAs, GaAlS, GaP, GaAlP, GaAlAsP, InGaAsP, GaN, InGaN, or ZnSe. Any visible light source used for the one or more visible light sources 1001b may produce any visible wavelength of light, although it is preferable that such visible light also be useful for causing fluorescent materials to be detected by use of the inspection lamp 1000 in addition to the ultraviolet LEDs 1001a producing radiation that is useful for this purpose.

Alternatively, the inspection lamp 1000 can have at least one LED 1001a that produces radiation useful for causing fluorescence while at least one different light source 1001b, whether LED or otherwise, produces radiation that is useful for determining what area is being illuminated by the inspection lamp 1000, even if the radiation produced by the one or more different light sources 1001b is essentially invisible. For example, the radiation produced by the one or more different light sources 1001b may produce an illumination pattern that is visible with an infrared camera.

As a further alternative, the inspection lamp 1000 may comprise at least one light source 1001a and at least one different light source 1001b, wherein such an inspection lamp is used to detect materials that do not fluoresce but absorb radiation produced by either but not both of the first said one or more light sources 1001a or second said one or more light sources 1001b. Such an alternative version of the inspection lamp 1000 may be used to detect materials that are not fluorescent but are illuminated differently by such an alternative inspection lamp 1000 than the background material that such materials to be detected would exist on. The material to be detected may appear a different color than the background material when illuminated by such an alternative form of the inspection lamp 1000.

The inspection lamp 1000 typically comprises additional parts such as an outer casing 1002, one or more batteries 1003, a switch 1004, a front lens 1005, a circuit board 1006, current limiting circuitry 1007, one or more wires 1008 connected to the switch 1004, and one or more wires or other pieces of conductive material 1009 for connecting to the one or more batteries 1003. A spring 1010 may be provided for making contact with any of the one or more batteries 1003. The outer casing 1002 may have a closed loop formation 1011 to attach a lanyard to. Other arrangements for the inspection lamp 1000 are foreseeable.

The lens 1005 may be a planar lens or it may be designed to affect the radiation from the ultraviolet LEDs 1001a and/or the visible light from the visible light source 1001b. The lens may comprise an arrangement of lens elements that collimate the light from the light sources 1001a, 1001b into a beam. Lens elements that form beams from any of the light sources 1001a, 1001b may be spherical convex lenses or aspheric convex lenses. Convex lens elements may be biconvex, planoconvex, or concavo-convex. Biconvex lens elements may have their two convex surfaces idential or non-identical. Non-identical convex surfaces of a lens element may have different degrees of curvature. Non-identical convex surfaces of a biconvex lens elements may differ in shape, for example one surface may be spherical while the other is aspheric. Any lens elements of the lens 1005 may be Fresnel lenses.

The current limiting circuitry 1007 is typically necessary for proper operation of the ultraviolet LEDs 1001a. The current limiting circuitry 1007 may be one or more resistors, one or more linear current regulator, one or more switching current regulators, or one or more boost converters. If a boost converter or other circuit depending on switching of inductors or capacitors is used, typically but not necessarily only one circuit is used no matter how many ultraviolet LEDs 1001a are provided. The one or more sources 1001b may or may not receive power from the current limiting circuitry 1007 that the ultraviolet LEDs 1001a receive power from. Separate circuitry may be used to limit the current that flows through the one or more visible light sources 1001b.

Figure 11:
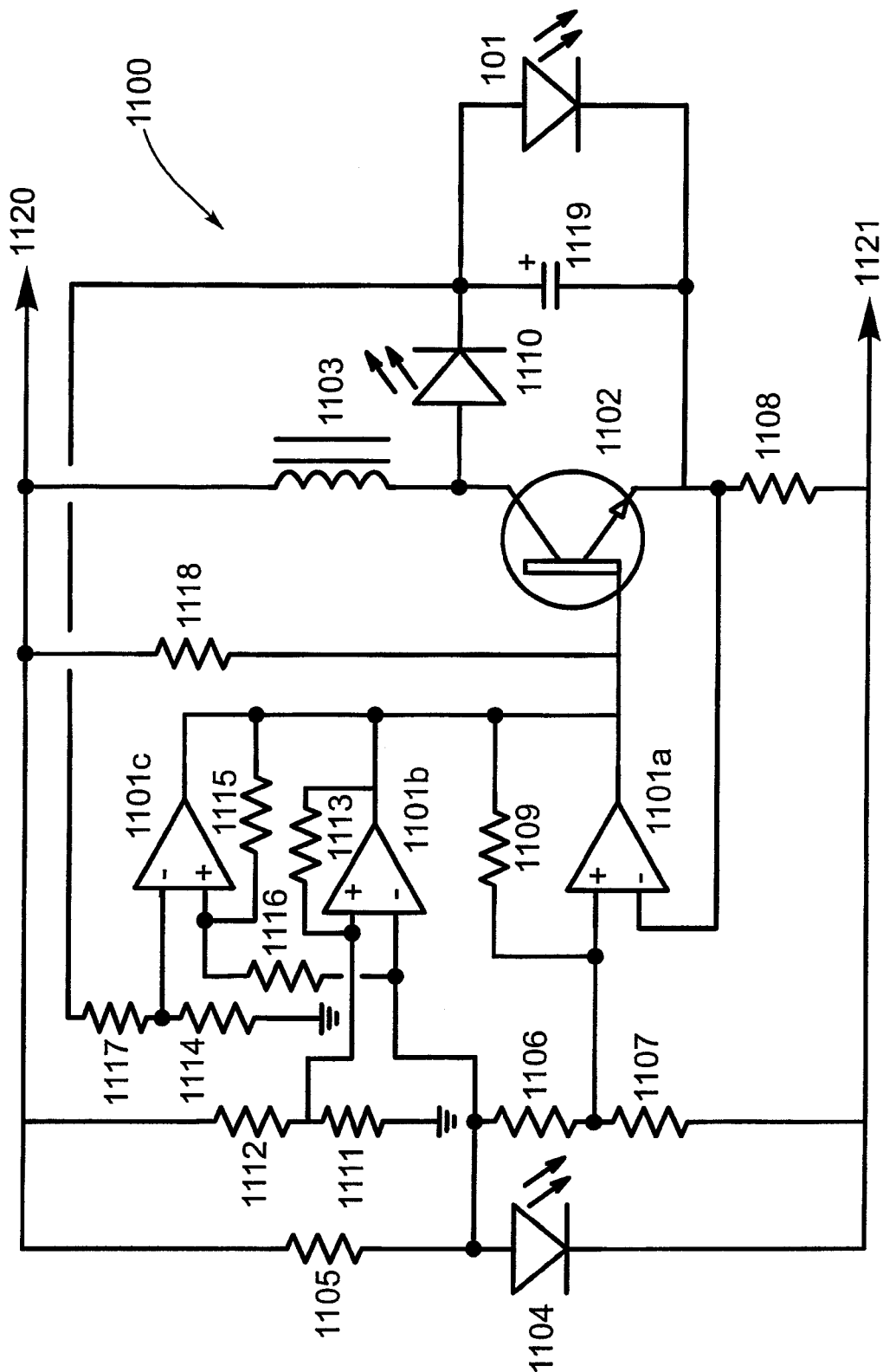
FIG. 11 is a schematic circuit diagram of a first circuit that may be used in the present invention.

Referring to FIG. 11, a boost converter circuit 1100 suitable for use with LEDs is provided in the present invention. The positive power wire (not shown) connects to the positive power connection point 1120. The negative power wire (not shown) is connected to the negative power connection point 1121. In the preferred embodiment of the present invention, the supply voltage is nominally 4.8 volts, as obtained from a battery having four NiMH cells in series. Other supply voltages can be used in various embodiments of the present invention.

Ground refers to the negative power supply connection 1121.

A diode 1104 receives current through a dropping resistor 1105 and is used as a voltage reference source. In the preferred embodiment of the present invention, the diode 1104 is an LED. LEDs have a lower percentage change of voltage drop as temperature varies than most other diodes do, although various embodiments of the present invention could use a diode 1104 of a type other than an LED. It is forseeable that alternative embodiments of the invention can use a diode 1104 of a type other than an LED and current received by the diode can be limited by an alternative means to the dropping resistor 1105.

The voltage across the diode 1104 is divided to a reduced reference voltage by the voltage divider formed by the two resistors 1106 and 1107. This reduced reference voltage is connected to the non-inverting input of a comparator 1101a. It is forseeable that in alternative embodiments of the present invention that the anode of the diode 1104 is connected directly to the non-inverting input of the comparator 1101a and the resistors 1106 and 1107 are omitted.

Power supply connections for the comparators 1101a, 1101b and 1101c are not shown for simplicity but are provided.

The comparator 1101a compares the reference voltage received by its non-inverting input with the voltage across the current sensing resistor 1108, the ungrounded end of which is connected to the inverting input of the comparator 1101a. A positive feedback resistor 1109 causes the comparator 1101a to have a hysteresis characteristic. Because of the positive feedback, the output of the comparator 1101a, if high, will switch to low if the voltage across the current resistor is significantly greater than that would be delivered to the non-inverting input of the comparator 1101a by the voltage divider comprising the two resistors 1106 and 1107 if the positive feedback resistor 1109 did not exist. The output of the comparator 1101a remains low until the voltage across the current sense resistor 1108 decreases to a voltage significantly less than that would be delivered to the non-inverting input of the comparator 1101a by the voltage divider comprising the two resistors 1106 and 1107 if the positive feedback resistor 1109 did not exist.

If the voltage divider comprising the resistors 1106 and 1107 is omitted, then an input resistor (not shown) would be connected from the anode of the diode 1104 to the non-inverting input of the comparator 1101a so that the hysteresis function of the comparator circuit using the comparator 1101a will function.

The output of the comparator 1101a is alternatively high or low in order to keep the voltage across the current sensing resistor 1108 close to the voltage delivered to the non-inverting input of the comparator 1101a. When power is first applied, the initial current through the inductor 1103 and the current sensing resistor 1108 is zero. As a result, the voltage across the current sensing resistor is initially zero. Since this makes the voltage of the inverting input of the comparator 1101a lower than the voltage of its non-inverting input, the output of the comparator 1101a is high and accordingly it turns a transistor 1102 on. This results in the supply voltage, minus any voltage drop in the transistor 1102 and the current sensing resistor 1108, to be applied to the inductor 1103 in order to increase the current flowing through the inductor 1103 and the current sensing resistor 1102. When the voltage across the current sensing resistor 1108 exceeds the voltage with respect to ground at the non-inverting input of the comparator 1101a, the comparator switches to its low state and turns the transistor 1102 off. Once this occurs, current flowing through the inductor 1103 continues to flow but does so through the diode 1110 and the LED 101. As long as the combined voltage drops of the LED 101 and the diode 1110 and that resulting from this current multiplied by the resistance of the inductor 1103 exceed the power supply voltage, the current will decrease. When this current decreases sufficiently for the voltage across the current sensing resistor to become less than the voltage with respect to ground of the non-inverting input of the comparator 1101a, the output of the comparator 1101a becomes high. This operation is a repeating cycle.

This cyclic operation attempts to regulate the current that flows through the current sensing resistor 1108 and accordingly through the inductor 1103. Ideally, this quantity of current multiplied by the supply voltage is the quantity of power delivered to the LED 101. Losses from this, which are to be minimized in ways known to those skilled in the art of designing and constructing switching power supply circuits, are small compared to the power delivered to the LED 101 if they are appropriately minimized. Accordingly, the amount of power delivered to the LED 101 is the supply voltage multiplied by the regulated average value of the current flowing through the current sensing resistor 1108, minus said losses. This means that the power delivered to the LED 101 will vary roughly proportionately with the supply voltage. Since the voltage delivered by most rechargeable batteries is usually relatively constant for most of the time that such batteries are discharging into a load, the amount of power delivered to the LED 101 is essentially regulated regardless of the voltage drop of the LED 101 as long as said voltage drop is high enough for the current flowing through the inductor 1103 to decrease when the transistor 1102 is off.

The transistor 1102 in the currently favored embodiment of the present invention is a power MOSFET of the logic level variety that is designed for use with supply voltages around 5 volts and less than 10 volts. Non-logic level MOSFETs can be used as the transistor 1102 if the power supply voltage is higher. In addition, the transistor 1102 can be a bipolar type, possibly a Darlington type. Such bipolar types require current input rather than voltage input, but will work in the boost converter as long as the pullup resistor 1118 supplies sufficient current for a bipolar version of the transistor 1102 to be on and as long as the comparator 1101a, when low, has an output voltage with respect to ground to ensure that such a bipolar version of the transistor 1102 is off.

A capacitor 1119 is provided in the preferred embodiment of the invention to filter or smooth the pulsating current that flows through the diode 1110 into a more nearly steady direct current flowing through the LED 101. Usually but not necessarily, such smoothing or filtering favorably affects the efficiency of the LED 101. It is forseeable that in alternative embodiments of the present invention, the capacitor 1119 is omitted, especially should the LED 101 be of a type that has efficiency increased by having a pulsating current waveform with higher instantaneous current as opposed to a steadier current having a lower peak instantaneous value.

With continuing reference to FIG. 11, additional comparators 1101b and 1101c are employed in the boost converter circuit of the currently preferred embodiment of the present invention. These additional comparators are typically but not necessarily comprised in the same integrated circuit package as the comparator 1101a.

In the currently preferred embodiment of the invention, the comparator 1101b is used to protect the boost converter circuit from ill effects of insufficient supply voltage and the comparator 1101c is used to protect the boost converter circuit from ill effects of excessive output voltage that would result if the LED 101 is disconnected or fails in a way where it becomes an open circuit.

The comparator 1101b is low if it senses insufficient supply voltage. The supply voltage is divided to a lower voltage determined by the voltage divider comprising the resistors 1111 and 1112. A positive feedback resistor 1113 with a large value is typically but not necessarily employed to add hysteresis to the function of the comparator 1101b for stabilization purposes. Such a divided voltage derived from the point where the resistors 1111 and 1112 connect to each other is compared to the voltage across the diode 1104. If the divided supply voltage presented to the non-inverting input of the comparator 1101b is less than the voltage across the diode 1104, then the comparator 1101b is low and prevents the transistor 1102 from being on. This can be desirable since otherwise with insufficient supply voltage the transistor 1102 can be only partially on when it is supposed to be on, and in such a case may be unable to pass the current it should conduct without an excessive voltage drop. Such an excessive voltage drop multiplied by the current conducted by the transistor 1102 may be an amount of power that overheats the transistor 1102 if the boost converter is not disabled by excessively low supply voltage.

The comparator 1101c is used to detect excessive output voltage that would typically result from the LED 101 being disconnected or failing in a way where it becomes an open circuit. A voltage divider comprising two resistors 1114 and 1117 It is easiest to combine the outputs of the comparators 1101b and 1101c with each other and the output of the comparator 1101a if the comparators are of the open collector type. In such a preferred case, the outputs of the comparators 1101a, 1101b, and 1101c are connected to each other and to the gate of the transistor 1102. In such a case, it is necessary in addition to have the pullup resistor 1118 so that the gate of the transistor 1102 is high if all of the comparators used are high. The circuitry becomes more complicated if more than one comparator is employed and the comparators are not of an open collector or open drain type. Such more complicated circuitry would typically employ means to AND the outputs of comparators that are not of an open collector or open drain type. Such more complicated circuitry employed to utilize more than one comparator element of a type that is not open collector nor open drain shall be considered alternative embodiments of the boost converter provided by at least one aspect of the present invention.

Figure 12:
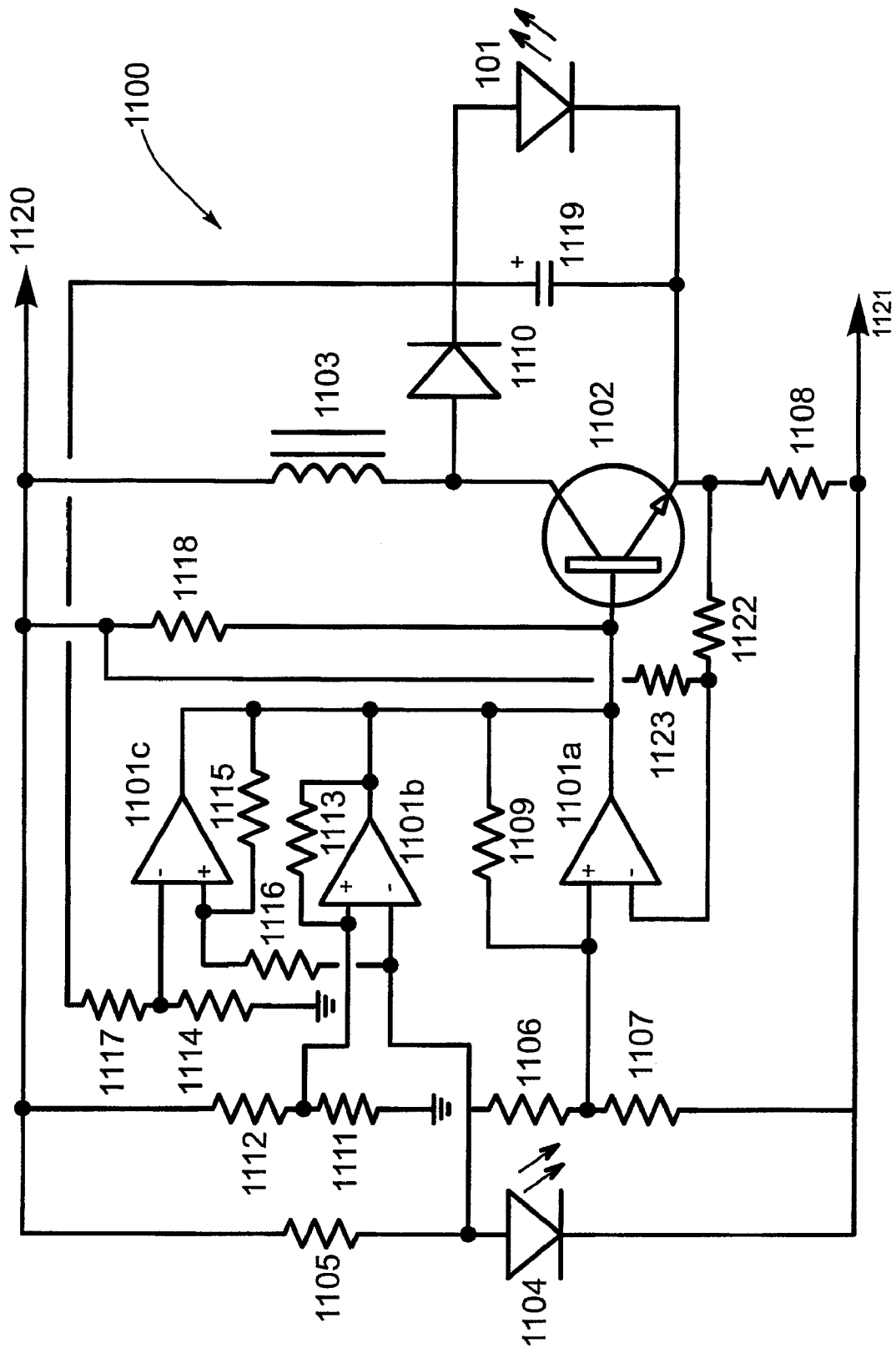
FIG. 12 is a schematic circuit diagram of a second circuit that may be used in the present invention.

Referring to FIG. 12, the boost converter circuit 1100 has additional resistors 1122 and 1123. These additional resistors are employed to have the comparator sense not just the voltage across the current sensing resistor 1108 but a combination of the supply voltage and the voltage across the current sensing resistor 1108.

The purpose is to cause the essentially regulated current flowing through the current sensing resistor 1108 to decrease as the supply voltage increases, in order to accomplish having the power delivered to the LED 101 not increase roughly proportionately with the supply voltage. As a result with appropriate values for the resistors 1122 and 1123, the power delivered to the LED 101 can be essentially constant with respect to varying power supply voltage as long as the power supply voltage is within a forseeable expected useful range.

Power supply connections to the comparators 1101a, 1101b and 1101c are not shown.

Figure 13:
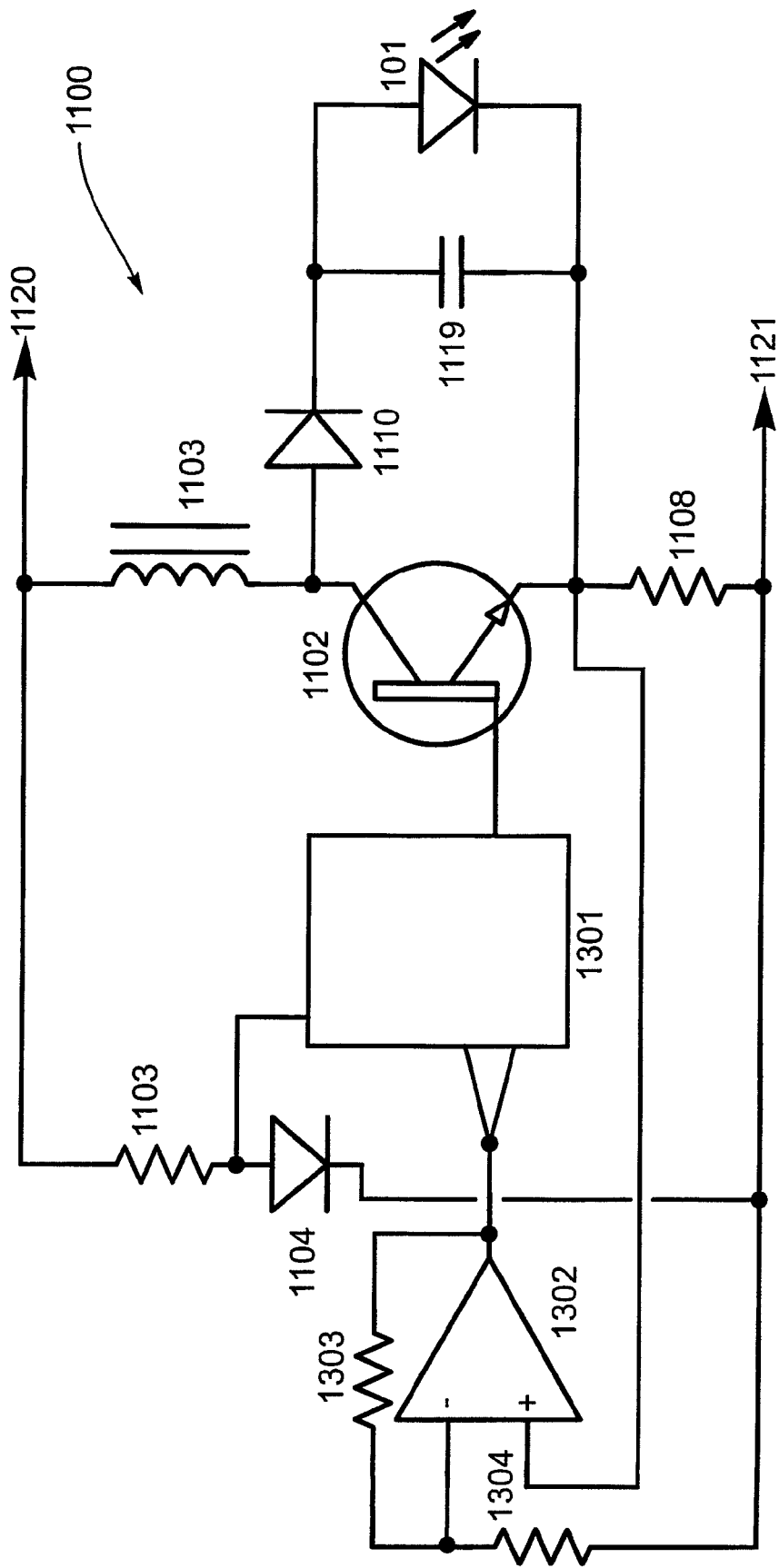
FIG. 13 is a schematic circuit diagram of a third circuit that may be used in the present invention.

Referring to FIG. 13, the boost converter circuit 1100 can be modified by having a 555 timer 1301 and an operational amplifier 1302 in lieu of the comparator 1101a. The anode of the voltage reference diode 1104 is connected to the control voltage pin of the 555 timer 1301. The trigger and threshold pins of the 555 timer 1301 are connected together, which makes the 555 timer a Schmidt trigger inverting buffer. The voltage across the current sense resistor 1108 is amplified by the operational amplifier 1302 to an extent determined by the feedback network comprising two resistors 1303 and 1304. When the amplified voltage from the output of the operational amplifier 1302 is less than half the voltage across the diode 1104, the 555 timer 1301 is high and turns the transistor 1102 on. The 555 timer remains high until the voltage presented to its trigger and threshold pins exceeds that presented to its control voltage pin. When the amplified voltage from the output of the operational amplifier 1302 exceeds the voltage across the diode 1104, then the 555 timer 1301 switches to its low state and turns the transistor 1102 off. The 555 timer 1301 returns to its high state when the voltage presented to its trigger and threshold pins by the operational amplifier 1302 decreases to half the voltage presented by the diode 1104 to the control voltage pin of the 555 timer 1301.

Otherwise, operation is like that of the boost converter circuit 1100 described in FIGS. 2 and 3. Comparators or additional operational amplifiers used as comparators may be employed to function like the comparators 1101b and 1101c shown in FIGS. 2 and 3 to protect the transistor 1102 and the diode 1110 from excessive output voltage and to prevent the boost converter circuit 1100 from operating if the power supply voltage is insufficient.

Power supply connections to the 555 timer 1301 and the operational amplifier 1302 are not shown. The reset pin of the 555 timer 1301 is normally connected to the positive power supply connection 1120, but may be connected otherwise so as to be essentially connected to the negative power supply connection 1121 instead as a result of additional circuitry detects insufficient supply voltage or excessive output voltage. Such additional circuitry would typically be similar to that comprising the comparators 1101b and 1101c shown in FIGS. 2 and 3. Such additional circuitry may use comparators or operational amplifiers. Such additional operational amplifiers may be but is not necessarily comprised in the same integrated circuit package as the operational amplifier 1302.

Other timer integrated circuits similar to the 555 can be used in lieu of a 555 for the timer integrated circuit 1301. Other variations of the boost converter circuit 1100 may be developed, using integrated circuits other than comparators and timers that resemble the 555.

Figure 14:
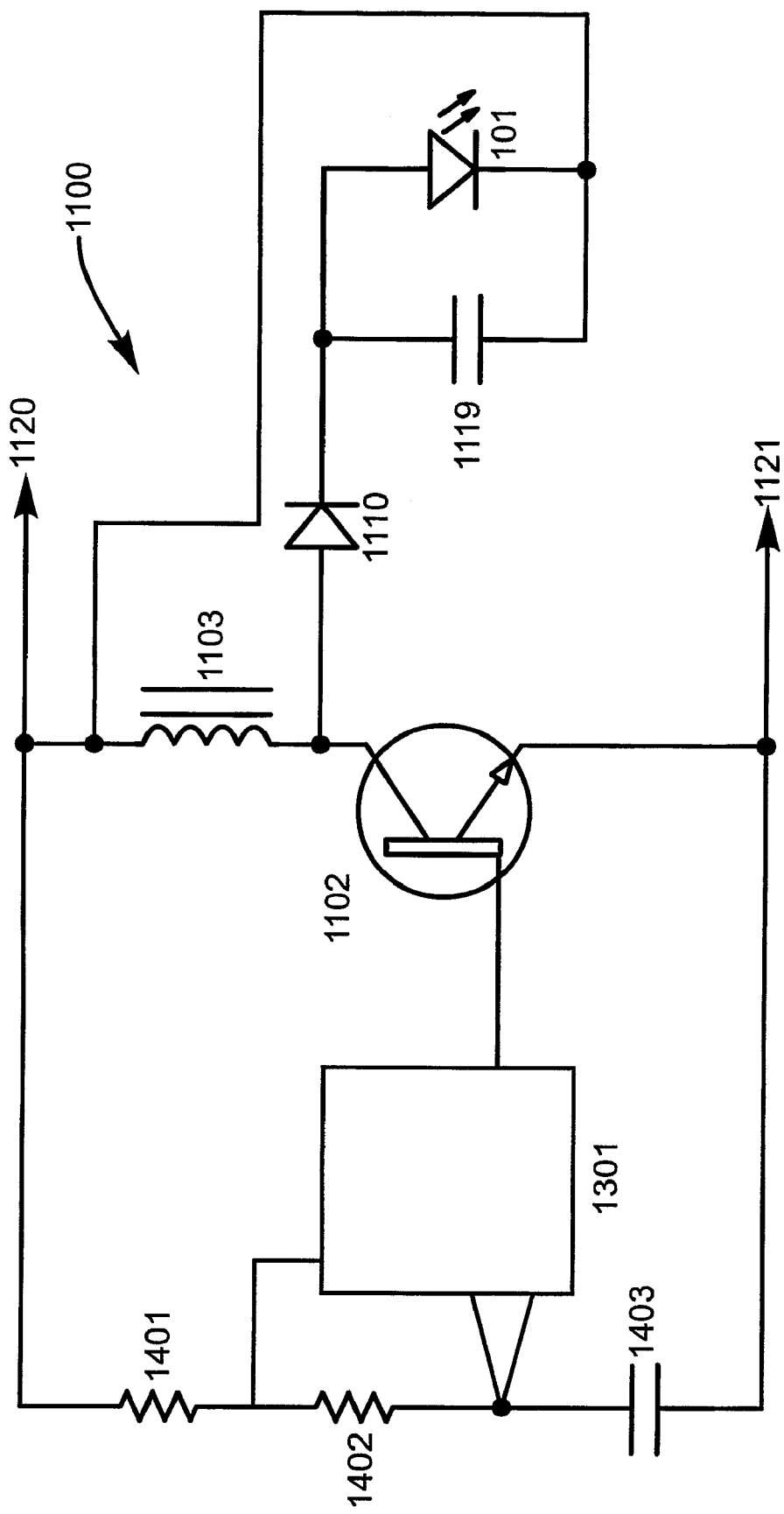
FIG. 14 is a schematic circuit diagram of a fourth circuit that may be used in the present invention.

Referring to FIG. 14, a simpler and less efficient variation of the boost converter circuit 1100 can be used in the present invention. This simpler boost converter circuit 1100 uses a 555 timer 1301 connected as an oscillator. The oscillator shown is the traditional astable 555 circuit and comprises the 555 timer 1301, resistors 1401 and 1402, and a timing capacitor 1403. A first resistor 1401 is connected from the positive power connection 1120 to the discharge pin of the 555 timer 1301. A second resistor 1402 is connected from the discharge pin of the 555 timer 1301 to the trigger and threshold pins of the 555 timer 1301. The trigger and threshold pins of the 555 timer are connected to each other. A timing capacitor 1403 is traditionally connected from the trigger and threshold pins of the 555 timer 1301 to the negative power supply connection 1121, but could be connected to the positive power connection 1120 instead. Values of the resistors 1401 and 1402 and the capacitor 1403 would be selected for the 555 timer 1301 to be high and low for appropriate amounts of time. In this implementation of the boost converter circuit 1100, the 555 timer is normally high for a greater amount of time than it is low.

In an alternative implementation of the astable 555 oscillator, the resistor 1401 can be omitted and the resistor 1402 can be connected from the trigger and threshold pins of the 555 timer 1301 to the output of the 555 timer 1301 instead of to the discharge pin of the 555 timer 1301.

No current sensing resistor is used.

A capacitor (not shown) may be connected from the control voltage pin of the 555 timer 1301 to either the negative power supply connection 1121 or the positive power supply connection 1120. Said capacitor is not necessarily employed.

When the output of the 555 timer 1301 is high, the transistor is on and essentially connects the inductor 1103 across the power supply connections 1120 and 1121. Current flowing through the inductor increases. When the output of the 555 timer is low, the transistor is off and current flowing through the inductor 1103 flows through the LED 101. Said current flowing through the LED 101 can be filtered or smoothed by the capacitor 1119.

Ideally, the 555 should be low long enough for the current flowing through the inductor 1103 to decrease to zero before the 555 becomes high again. Otherwise the current flowing through the inductor 1103 can increase to an excessive value. It is forseeable that further variations of this variation of the boost converter circuit 1100 can be made that operate satisfactorily if the current flowing through the inductor 1103 does not decrease to zero before the transistor 1102 is turned on to resume increase of said current flowing through the inductor 1103.

There are possible improvements to this variation of the boost converter circuit 1100, such as having the negative leads of the LED 101 and the capacitor 1119 connected to the negative power supply connection 1121 instead of the positive power supply connection 1120. This would have the power supply voltage assist current flowing through the LED 101 when the current flowing through the inductor 1103 is forced through the LED 101 by the transistor 101 being off. If the voltage required to operate the LED 101 is less than twice the power supply voltage, then with this improvement it will typically be necessary to have the transistor 1102 off for a greater amount of time than the transistor 1102 is on. Although it is forseeable that off time insufficiently long for the current flowing through the inductor 1103 to decrease to zero, it is apparent that it would be preferable to shorten the on time, lengthen the off time or both if necessary for the current flowing through the inductor 1103 to decrease to zero while the transistor 1102 is off. This can be achieved by adding an inverting buffer between the output of the 555 timer 1301 and the transistor 1102. Said inverting buffer can be achieved with a second 555 timer. Said second 555 timer may be packaged with the 555 timer 1301 in a single integrated circuit package such as a 556. Timer integrated circuits other than the 555 and 556 may be found to be usable.

An oscillator other than one based on a 555 timer can be used. Such oscillators include but are not limited to ones based on operational amplifiers, ones based on comparators, astable multivibrators, Schmidt trigger oscillators using a device other than a 555 timer as a Schmidt trigger, and function generator integrated circuits used to produce a square wave.

Figure 15:
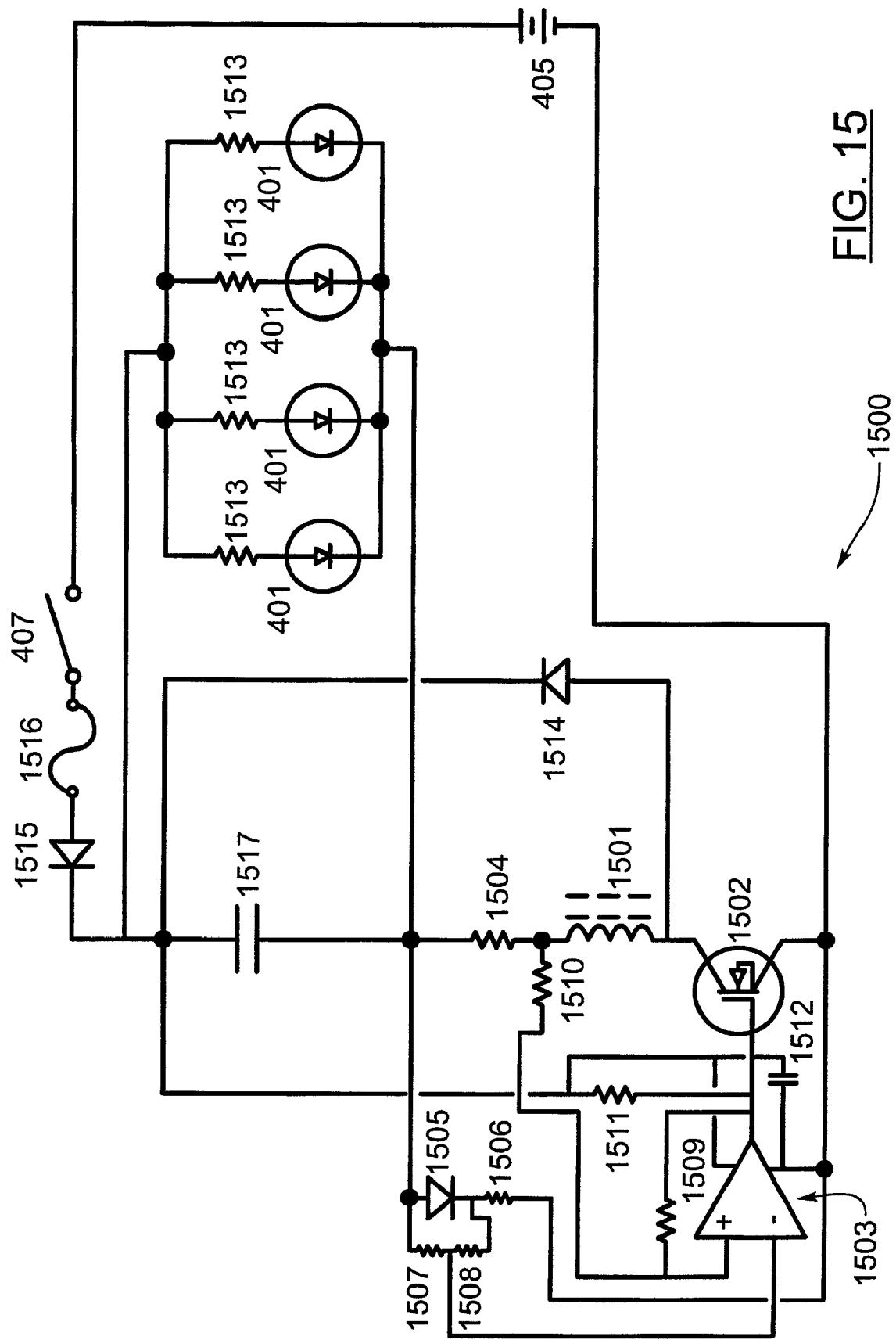
FIG. 15 is a schematic circuit diagram of a fifth circuit that may be used in the present invention.

Referring to FIG. 15, an LED inspection lamp can have a switching current regulator circuit 1500 that enables the LEDs 401 to receive a quantity of current that does not vary significantly with the battery voltage, as long as the battery voltage significantly exceeds the minimum voltage required to cause the desired amount of current to flow through the LEDs 101. The shown switching regulator 1500 comprises a comparator 1503, an inductor 1501, a switching transistor 1502, diodes 1505, 1514, and 1515, resistors 1504, 1506, 1507, 1508, 1509, 1510 and 1511, and capacitors 1512 and 1517.

The comparator 1503 compares the voltage drops across two resistors 1507 and 1504. One lead of the resistor 1504 is connected to one lead of the resistor 1507, and this enables comparing the voltages of the other leads of these two resistors with respect to ground or the negative battery terminal. Of these two resistors, the resistor 1504 is a current sensing resistor that has a voltage drop that is nearly enough proportional to the magnitude of the current flowing through LEDs 401.

Assuming the power supply voltage exceeds the combined normal voltage drops of one of the LEDs 401 and the diode 1505, current will flow through the resistor 1506. The diode 1505 is used for a voltage reference and the resistor 1506 is provided in order for a small quantity of current to flow through the diode 1505. A voltage divider comprising the resistors 1507 and 1508 provides a divided reference voltage that is compared with the voltage across the current sensing resistor 1504.

The voltage divider resistors 1507 and 1508 should have sufficiently high values and the resistor 1506 should have a sufficiently low value such that most of the current flowing through the resistor 1506 flows through the diode 1505 rather than through the voltage divider resistors 1507 and 1508. This provides for a voltage across the resistor 1507 being nearly constant, and equal to the voltage drop of the diode 1505 times the value of the resistor 1507 divided by the sum of the values of the resistors 1507 and 1508.

When power is initially applied, the magnitude of the current flowing through the inductor 1501 and the current sensing resistor 1504 is zero. As a result, the voltage across the current sensing resistor 1504 is zero. However, voltage will appear immediately across the resistor 1507. This results in the inverting input of the comparator 1503 being more negative than the non-inverting input of the same comparator, and so the output of the same comparator will be "high" and turn "on" the switching transistor 1502.

The switching transistor as shown is a power MOSFET. Other transistor types can be used for the switching transistor 1502, including MOSFETs other than power MOSFETs, insulated gate bipolar transistors, and conventional bipolar transistors. If the switching transistor 1502 is a conventional bipolar transistor and the comparator 1503 is not of an "open collector" or "open drain" type, then it is typically necessary to add a resistor (not shown) in series with the base terminal of a conventional bipolar transistor being used as the switching transistor 1502.

When the switching transistor 1502 is "on" or conductive, assuming the power supply voltage is sufficient, current will flow through through the LEDs 401, the current sensing resistor 1504, the inductor 1501 and the switching transistor 1502. The current will increase at a rate equal to the voltage across the inductor divided by the value of the inductor. The voltage across the inductor is the supply voltage minus the voltage drops of the LEDs 401 and other components that current flowing through the inductor 1501 has to flow through, such as any protection diode 1515, current dividing resistors 1513, the current sensing resistor 1504 and the switching transistor 1502.

The current flowing through the inductor 1501 increases and will normally increase to an extent such that the voltage drop of the current sensing resistor 1504 exceeds the voltage across the resistor 1507.

When that happens, the output of the comparator 1503 will switch to its "low" state and turn "off" the switching transistor 1502.

When the switching transistor 1502 is "off" or nonconductive, current that is flowing through the inductor 1501 continues to flow and but does so through a closed loop comprising the inductor 1501, the current sensing resistor 1504, the LEDs 401 and a diode 1514. With no power supply in this closed loop, the magnitude of this current will decrease. Once this current decreases to an extent such that the voltage drop of the current sensing resistor 1504 is less than the voltage across the resistor 1507, the output of the comparator will go "high" again and the switching transistor 1502 will be switched "on" again. The magnitude of the current flowing through the current sensing resistor will alternately increase and decrease but will normally always be close to that necessary to cause the voltage drop of the current sensing resistor 1504 to be close to the voltage across the resistor 1507.

As a result, the magnitude of the current flowing through the current sensing resistor 1504, which is nearly all of the current flowing through the LEDs 401, is essentially regulated.

Resistors 1509 and 1510 are provided to provide a small amount of positive feedback to the non-inverting input of the comparator 1503 from the output of the same comparator. This allows the magnitude of the current flowing through the current sensing resistor to change by some significant extent before the comparator 1503 changes states. This is typically necessary for the switching transistor 1502 to spend nearly all of the time of each switching cycle being either fully conductive or fully nonconductive.

When the switching transistor 1502 is "on" or conductive, nearly all of the current being consumed by the circuit 1500 from the battery 405 is flowing through the LEDs 401. When the switching transistor 1502 is "off" or nonconductive, the current flowing through the LEDs 401 is not being drawn from the battery 405. At that time, the only current being drawn from the battery 405 is that necessary for the comparator 1503 to function. As a result, the average current being drawn from the battery 405 is normally less than the current flowing through the LEDs 401. This is an advantage of a switching current regulator 1500 over "linear" or non-switching current regulator circuits that would normally result in current consumption from the battery 405 to be at least as great as the current flowing through the LEDs 401.

The switching regulator 1500 also comprises a pullup resistor 1511 if the comparator 1503 is an "open collector" or "open drain" type. A capacitor 1512 may be provided across the power supply terminals of the comparator 1503 to absorb any switching-related transients in the supply voltage to the comparator 1503. A filter capacitor 1517 may be provided to make the magnitude of the current flowing through the LEDs 401 more constant throughout each cycle of the increase and decrease of the magnitude of the current flowing through the current sensing resistor 1504. A diode 1515 may be provided to protect the circuit 1500 from being damaged should the battery 405 be connected with reversed polarity. Such a diode 1515 may be a Schottky diode since Schottky diodes have a lower voltage drop than most other diodes do. A fuse 1516 may be provided to prevent catastrophic failure should the circuit 1500 malfunction. A switch 407 is typically provided to turn on and off the circuit 1500. Current dividing resistors 1513 may be necessary if more than one LED 401 is used and the LEDs 401 are to be connected essentially in parallel with each other.

An inspection lamp having the shown components of the switching current regulator circuit 1500 may have additional components (not shown) including but not limited to a battery status indicator lamp. Such a battery status indicator lamp may be controlled by a voltage comparator circuit that uses a comparator in the same integrated circuit package as the comparator 1503.

Figure 16:
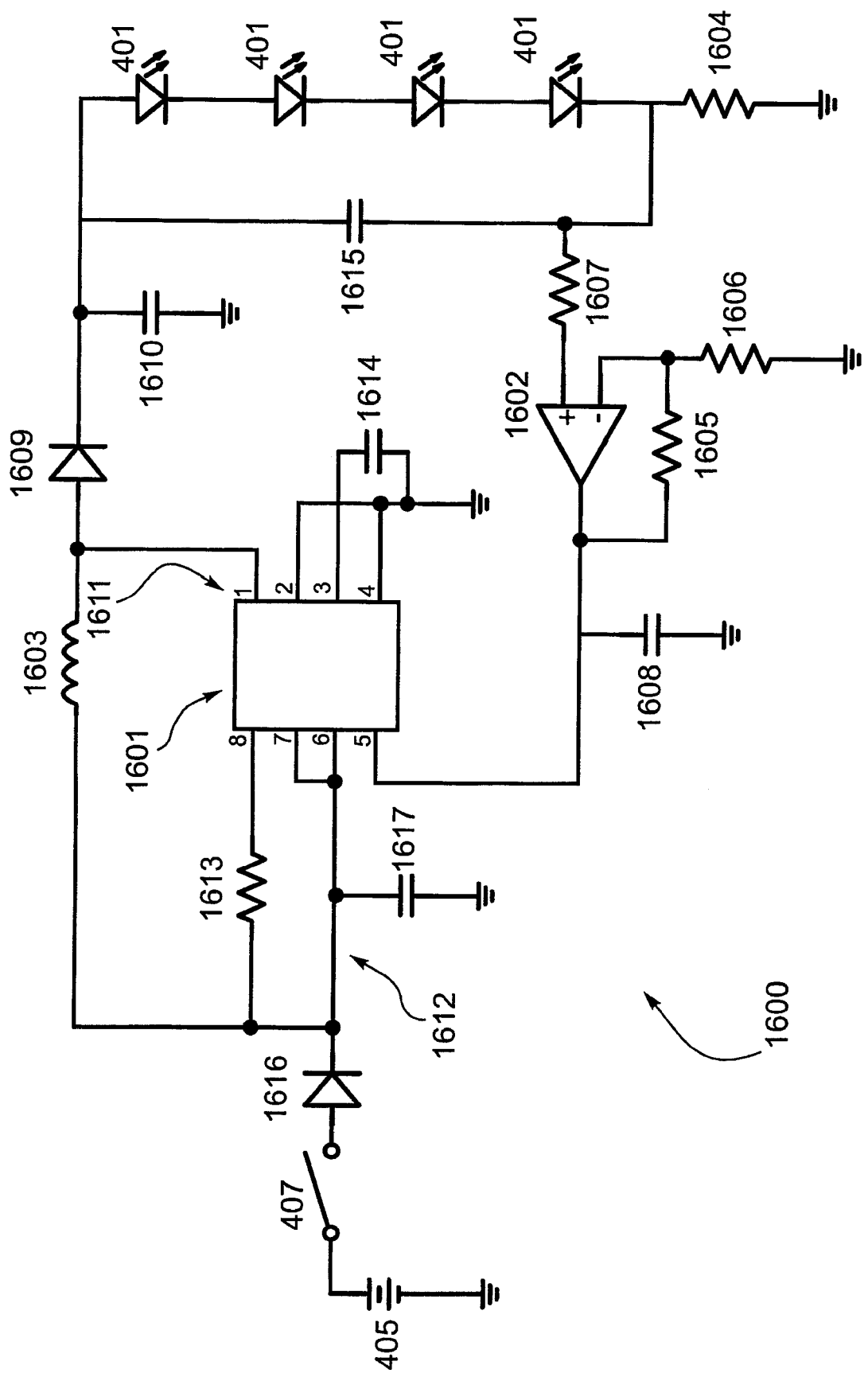
FIG. 16 is a schematic circuit diagram of a sixth circuit that may be used in the present invention.

Referring to FIG. 16, an LED inspection lamp can have a boost converter circuit 1600 that is suitable for LED flashlights and LED inspection lamps having an LED 401 or series string of LEDs 401 requiring a greater voltage than is available without a boost converter.

The boost converter can be a current-regulating boost converter. The circuit of FIG. 16 is such a current-regulating boost converter, found to adequately deliver regulated current through a series string of LEDs 401 when the supply voltage is anywhere from 4.5 to 10 volts.

The current regulating boost converter 1600 shown in FIG. 16 has an integrated circuit 1601 that is of a type suitable for such purposes in LED flashlights, and said integrated circuit 1601 may be but is not necessarily a "PJ34063CS" type.

A boost converter circuit 1600 typically requires an inductor 1603. The value of the inductor 1603 is typically but not necessarily 47 to 100 microhenries. The inductor 1603 has a requirement of not saturating at the peak current that it is required to conduct, which is typically but not necessarily approaching twice the ratio of total LED power to the voltage drop across the LED or series string thereof 401. A suitable inductor 1603 typically has a ferrite core that is gapped or is made of a low permeability material in order to minimize the overall size of a core that does not saturate. The core material is typically nonconductive in order to minimize eddy current losses in the core. An inductor 1603 having a rod style core will work but generally the inductor can be made smaller with a gapped core than with a rod style core.

A battery 405 is shown, which is of a "9 volt alkaline" "transistor radio" type, although other types including rechargeable types could be used in alternative embodiments of the present invention.

A switch 407 is provided to turn on/off the circuit 1600. Preferably the switch 407 is a pushbutton type that is usable both as a momentary switch (by pushing "halfway down") and as an "on/off" switch by pushing with greater force.

A current sensing resistor 1604 is provided for sensing the magnitude of the current that is flowing through the LEDs 401. An operational amplifier 1602 and associated gain-determining resistors 1605 and 1606 are provided to supply to the integrated circuit 1601 a feedback of the magnitude of the current that is flowing through the LEDs 401 and the current sensing resistor 1604. The resistor 1607, having a value close to that which would be achieved by paralleling the resistors 1605 and 1606, is provided so that the two inputs of the operational amplifier 1602 receive as equally as possible any effects of the input currents produced by the operational amplifier 1602. A capacitor 1608 is provided for filtering that the integrated circuit 1601 may require of the feedback signal. It is foreseeable that the circuit 1600 may be made to work satisfactorily without the resistor 1607 and the capacitor 1608.

The operational amplifier 1602b and its associated circuitry form an amplifier that amplifies the voltage across the current sensing resistor 1604. When the output voltage of the operational amplifier 1602b exceeds approx. 1.6 volts, the integrated circuit 1601 shuts down until the output voltage of the operational amplifier 1602b decreases slightly.

The integrated circuit 1601 includes a switching transistor. The collector lead of the switching transistor is connected to a collector lead 1611 of the integrated circuit 1601. The collector lead 1611 is connected to one lead of the inductor 1603, while the other lead of the inductor 1603 is connected to the main positive power supply point 1612 of the circuit 1600. Pulsating direct current at a voltage higher than that of the voltage of the battery 405 is achieved from the switching transistor repeatedly interrupting the current that is flowing through the inductor 1603. This pulsating higher voltage is received from the collector lead 1611 and filtered into steady direct current by a diode 1609 and a filter capacitor 1610. The diode 1609 is required to keep the capacitor 1610 from discharging through the integrated circuit 1601 when the switching transistor inside the integrated circuit 1601 is on. The diode 1609 should be of a type that is suitable for the ultrasonic frequency of the pulsating direct current that is received from the collector lead 1611. The diode 1609 may be a Schottky diode.

In variations of the boost converter circuit 1600, the switching transistor can be a separate part (not shown) rather than a part of the integrated circuit 1601. The switching transistor, whether it is a separate part or a part of the integrated circuit 1601, may be a MOSFET. If the switching transistor is a MOSFET, then the transistor terminal that is connected to the inductor 1603 is referred to as a "drain" rather than as a "collector".

A resistor 1613 and capacitor 1614 are external parts that are required associated components of the circuitry inside the integrated circuit 1601. A capacitor 1615 in parallel with the series string of LEDs 301 is a low value capacitor that has been found to be beneficial for optimum operation of the circuit 1600, apparently by partially filtering the higher frequency harmonic content of the pulsating direct current received from the collector terminal 1611. The larger value filtering capacitor 1610 can have excessive inductance for filtering the highest frequencies that are present to a significant extent in said pulsating direct current.

A diode 1616 is provided to protect the circuit 1600 in case the battery 405 is connected with reversed polarity. It is preferred that the diode 1616 be a Schottky diode because Schottky diodes have a lower voltage drop than other commonly available diodes.

A capacitor 1617 is provided across the power supply rails of the circuit 1600 to reduce irregularities in the supply voltage that result from non-constant current draw through the impedance of the battery 405.

The boost converter circuit may be assembled on a circuit board that has additional circuitry. Such additional circuitry may include circuitry that controls a battery status indicator lamp.

Figure 17:
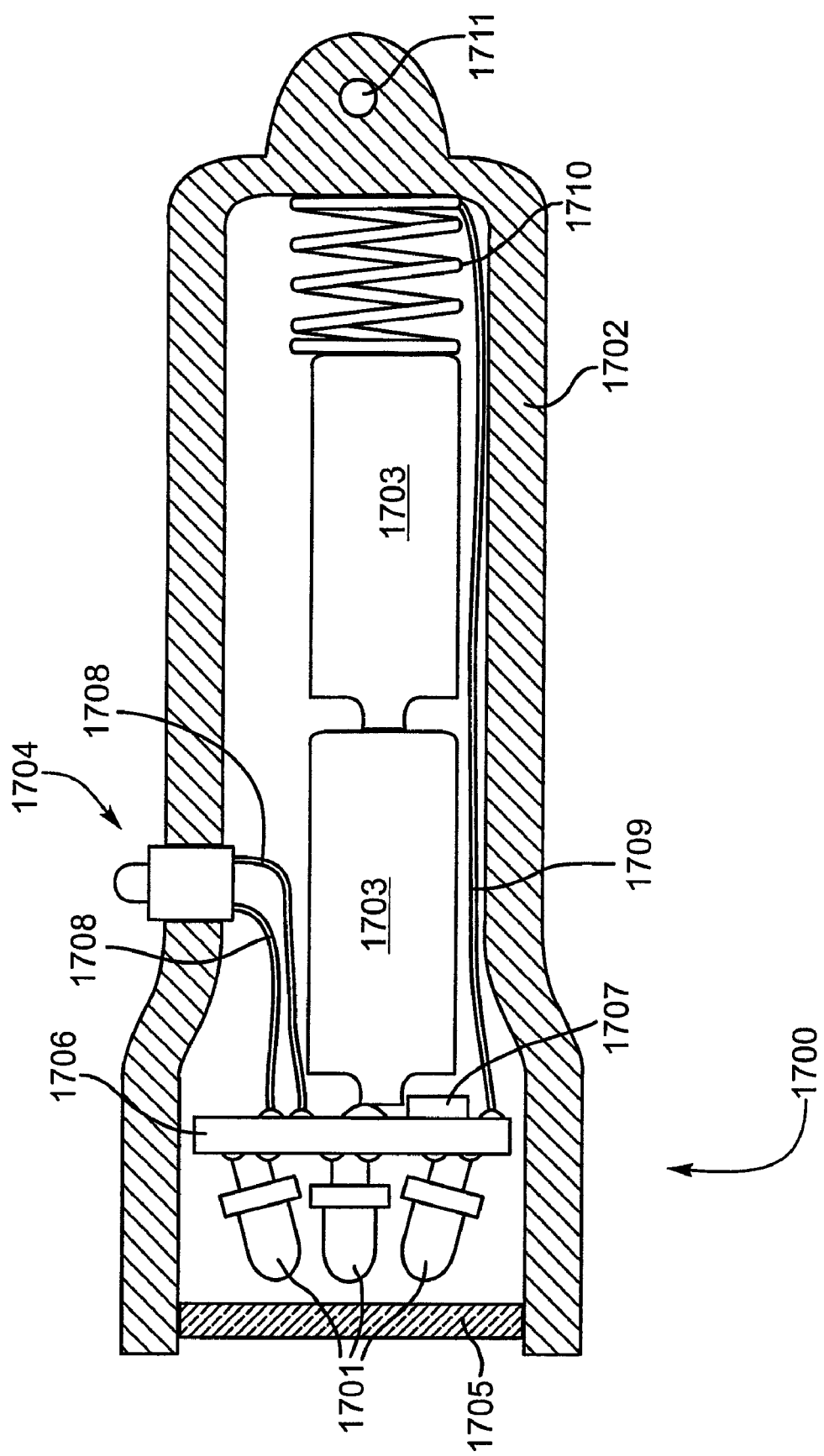
FIG. 17 is a cross sectional side view of a tenth embodiment of the present invention.

Referring to FIG. 17, a tenth embodiment of the present invention is an inspection lamp 1700 that has one or more LEDs 1701 that produce a beam of radiation that is suitable for causing fluorescence of materials to be detected by an inspection lamp, wherein the LEDs 1701 produce a beam that has a width of 10 degrees or less. This would typically be accomplished by making the LEDs 1701 of a narrow beam design and with a diameter of at least 7 millimeters. LEDs 1701 that have a diameter of 7.5 to 13 millimaters can easily produce a beam that is sufficiently narrow and intense.

The LEDs 1701 would typically produce radiation that has a peak wavelength of 395 to 415 nanometers in order to produce a beam that visibly illuminates the area being irradiated but is not so brightly visible as to overwhelm the visible fluorescence of fluorescent materials to be detected by using the inspection lamp 1700. The LEDs 1701 may alternatively have a shorter peak wavelength but produce an adequately visible beam due to having a peak wavelength only slightly less than 395 nanometers or by producing some visible light that is outside the wavelength range of an essentially visible main spectral band in the ultraviolet. Ultraviolet LEDs with typical peak wavelengths as short as 365 nm usually produce some radiation that is visible. Further alternatively, one or more of the LEDs 1701 may produce a visible beam while at least one other of the LEDs 1701 would produce essentially invisible radiation. The inspection lamp 1700 can also be made with LEDs 1701 that have a peak wavelength longer than 415 nanometers, although wavelengths longer than 415 nanometers but capable of causing fluorescence of visibly fluorescent materials will typically require a user of the inspection lamp 1700 to use a viewing filter such as tinted glasses that block most of the visible light produced by the inspection lamp 1700 but pass at least some of the light produced by fluorescent materials to be detected by using such an inspection lamp 1700.

The inspection lamp 1700 typically comprises additional parts such as an outer casing 1702, one or more batteries 1703, a switch 1704, a circuit board 1706, current limiting circuitry 1707, one or more wires 1708 connected to the switch 1704, and one or more wires or other pieces of conductive material 1709 for connecting to the one or more batteries 1703. A spring 1710 may be provided for making contact with any of the one or more batteries 1703. The outer casing 1702 may have a closed loop formation 1711 to attach a lanyard to. Other arrangements for the inspection lamp 1700 are foreseeable.

A front lens 1705 may be provided in the inspection lamp 1700 for purposes including any or any combination of the following purposes:

1. As part of making the inspection lamp 1700 waterproof.

2. To make the inspection lamp 1700 more attractive. For such a purpose, the lens 1700 may be a non-planar lens such as a convex or concave lens or a fresnel lens with a long focal length. Such a lens may comprise more than one lens element. Such a lens may have prismatic facets. If the lens 1705 has prismatic facets, then the LEDs 1701 would be aimed in directions such that their beams are projected into a desirable direction upon exiting the lens 1705. Any facets in the lens 1705 may be convex or concave in addition to being prismatic.

3. To diffuse the beam to a small extent to remove sharp irregularities in the beam. Such a diffusing lens may be textured, translucent and/or frosted.

4. As a filter that blocks undesirable wavelengths of radiation produced by the LEDs 1701, such as light that has wavelengths the same as or near the wavelengths of radiation produced by fluorescent materials to be detected by using the inspection lamp 1700.

If a lens 1705 is used and it is not planar, the lens 1705 or individual lens elements in the lens 1705 may be biconvex, planoconvex, concavo-convex, biconcave, planoconcave, or convexconcave. Any curved surfaces of the lens

1705 may be spherical, compound curves, or aspheric curves such as paraboloidal curves or ellipsoidal curves.

The current limiting circuitry 1707 is typically necessary for proper operation of the ultraviolet LEDs 1701. The current limiting circuitry 1707 may be one or more resistors, one or more linear current regulator, one or more switching current regulators, or one or more boost converters. If a boost converter or other circuit depending on switching of inductors or capacitors is used, typically but not necessarily only one circuit is used no matter how many ultraviolet LEDs 1701 are provided. The one or more t sources 1701 may or may not receive power from the current limiting circuitry 1707 that the ultraviolet LEDs 1701 receive power from. Separate circuitry may be used to limit the current that flows through the one or more visible light sources 1701.

Figure 18:
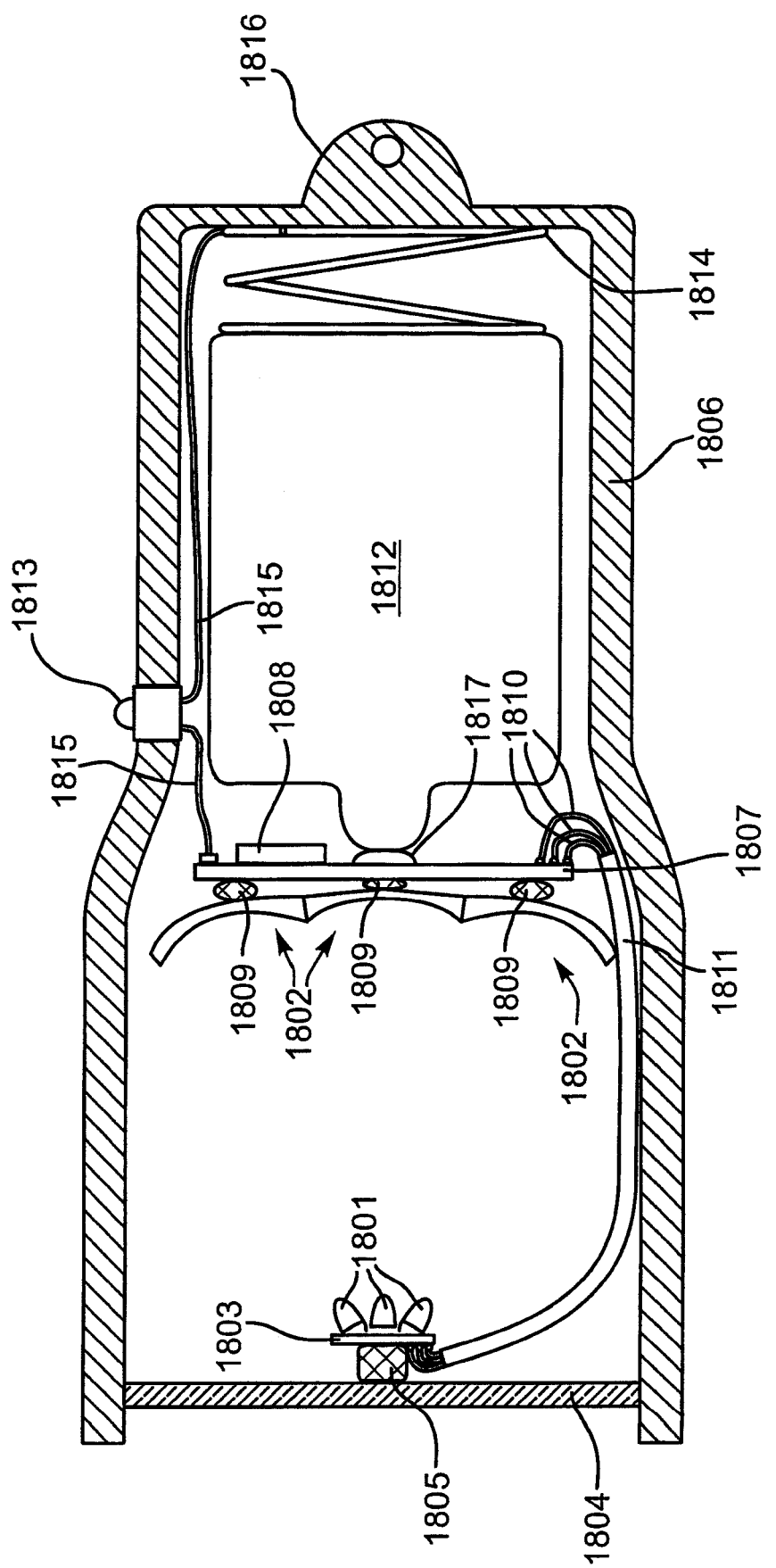
FIG. 18 is a cross sectional side view of an eleventh embodiment of the present invention.

Referring to FIG. 18, an eleventh embodiment of the present invention is an inspection lamp 1800 comprising two or more LEDs 1801 that are aimed rearward towards concave mirrors 1802 so that the concave mirrors 1802 collimate the radiation produced by the LEDs 1801 into a beam. Typically each of the LEDs 1801 is associated with a corresponding concave mirror 1802, and the number of concave mirrors 1802 would typically be the same as the number of LEDs 1801. Alternatively, it is foreseeable that an inspection lamp 1801 could be made to work with the number of concave mirrors 1802 being different from the number of LEDs 1801.

The concave mirrors 1802 are ideally ellipsoidal if they are to produce a beam that is well defined at short distances forward of the inspection lamp 1800. The concave mirrors 1802 are ideally paraboloidal if they are to produce a beam that is well defined at great distances forward of the inspection lamp 1800. Other shapes of curved surfaces of the concave mirrors 1802 may be found to work adequately, such as hyperboloidal or spherical shapes. The concave mirrors may have stepped surfaces like those of fresnel lenses. The concave mirrors 1802 may or may not comprise a plurality of flat facets. The concave mirrors 1802 may or may not be textured for purposes such as smoothing irregularities in the beams formed by them or for an attractive appearance.

The concave mirrors 1802 may or may not have a protective overcoating. If any concave mirror elements 802 have a protective overcoating, the protective overcoating may be silicon dioxide. Any protective overcoating on any concave mirrors 1802 may be a polymer. Any protective overcoating on any concave mirrors 1802 may be sprayed on or applied in a manner other than spraying, such as being applied with a paintbrush or similar means. Any protective coating may or may not require curing or solidification such as by evaporation of a solvent, inherent reaction of chemical ingredients in the protective coating, or oxidation or polymerization. Curing of any protective coating on any mirrors 1802 may or may not require or be assisted by irradation by ultraviolet radiation or other radiation. Any mirrors 1802 may or may not require elevated temperatures in their formation, such as for curing of any protective coating.

The LEDs 1801 would typically produce radiation that has a peak wavelength of 395 to 415 nanometers in order to produce a beam that visibly illuminates the area being irradiated but is not so brightly visible as to overwhelm the visible fluorescence of fluorescent materials to be detected by using the inspection lamp 1800. The LEDs 1801 may alternatively have a shorter peak wavelength but produce an adequately visible beam due to having a peak wavelength only slightly less than 395 nanometers or by producing some visible light that is outside the wavelength range of an essentially visible main spectral band in the ultraviolet. Ultraviolet LEDs with typical peak wavelengths as short as 365 nm usually produce some radiation that is visible. Further alternatively, one or more of the LEDs 1801 may produce a visible beam while at least one other of the LEDs 1801 would produce essentially invisible radiation. The inspection lamp 1800 can also be made with LEDs 1801 that have a peak wavelength longer than 415 nanometers, although wavelengths longer than 415 nanometers but capable of causing fluorescence of visibly fluorescent materials will typically require a user of the inspection lamp 1800 to use a viewing filter such as tinted glasses that block most of the visible light produced by the inspection lamp 1800 but pass at least some of the light produced by fluorescent materials to be detected by using such an inspection lamp 1800.

A front lens 1804 may be provided in the inspection lamp 1800 for purposes including any or any combination of the following purposes:

1. As part of making the inspection lamp 1800 waterproof.
2. To make the inspection lamp 1800 more attractive. For such a purpose, the lens 1800 may be a non-planar lens such as a convex or concave lens or a fresnel lens with a long focal length. Such a lens may comprise more than one lens element. Such a lens may have prismatic facets. If the lens 1804 has prismatic facets, then the concave mirrors 1802 would be aligned in a manner such that the beams formed by the concave mirrors 1802 are projected into a desirable direction upon exiting the lens 1804. Any facts in the lens 1804 may be convex or concave in addition to being prismatic.
3. To diffuse the beam to a small extent to remove sharp irregularities in the beam. Such a diffusing lens may be textured, translucent and/or frosted.
4. As a filter that blocks undesirable wavelengths of radiation produced by the LEDs 1701, such as light that has wavelengths the same as or near the wavelengths of radiation produced by fluorescent materials to be detected by using the inspection lamp 1800.

If a lens 1804 is used and it is not planar, the lens 1804 or individual lens elements in the lens 1804 may be biconvex, planoconvex, concavo-convex, biconcave, planoconcave, or convexconcave. Any curved surfaces of the lens 1804 may be spherical, compound curves, or aspheric curves such as paraboloidal curves or ellipsoidal curves.

The LEDs 1802 may be attached to an LED board 1803. The LED board 1803 may be a circuit board, a circuit board combined with a heatsink, or it may comprise a piece of material suitable for use as a heatsink.

The inspection lamp 1800 typically has an outer casing 1806 that typically has a distinct head section and handle section. As shown, the head section and handle section of the outer casing 1806 have a common longitudinal axis. Alternatively, the inspection lamp may have a head and handle with axes that are offset from each other or not parallel to each other. For example, a variation of the inspection lamp 1800 or of other inspection lamps shown herein may have a handle in the form of a pistol grip.

The LED board 1803 may, as shown, be attached to the front lens 1804 with glue 1805. Alternative means of mounting the LED board 1803 are foreseeable, such as connecting it to the outer casing 1806 with thin rods (not shown).

A circuit board 1807 is typically provided. The LEDs 1801 typically require current limiting circuitry 1808 that is mounted on the circuit board 1807. The current limiting circuitry 1808 is typically necessary for proper operation of the LEDs 1801. The current limiting circuitry 1808 may be one or more resistors, one or more linear current regulator, one or more switching current regulators, or one or more boost converters. If a boost converter or other circuit depending on switching of inductors or capacitors is used, typically but not necessarily only one circuit is used no matter how many LEDs 1801 are provided. The one or more LEDs 1801 may or may not receive power from the current limiting circuitry 1808 that the LEDs 1801 receive power from. Separate circuitry may be used to limit the current that flows through the one or more visible light sources 1801.

The concave mirrors 1802 may be attached to the circuit board 1807 by means of glue 1809. If the concave mirrors 1802 are attached to the circuit board 1807, either the concave mirrors 1802 or the circuit board 1807 may be mounted to the outer casing 1806. Other arrangements are foreseeable for holding the circuit board 1807 and the concave mirrors 1808 in their proper positions.

Wires 1810 are typically provided to supply power to the LEDs 1801. The wires 1810 may be comprised in a cable 1811.

The inspection lamp 1800 is typically powered by one or more batteries 1812, although alternatively the inspection lamp 1800 may receive power from an external power source. Any batteries 1812 may or may not be rechargeable.

The inspection lamp 1800 is shown with a switch 1813, a battery spring 1814, wires 1815, and a closed loop 1816 to attach a lanyard to. As shown, the circuit board 1807 may have a battery contact 1817. Other arrangements are foreseeable for alternative embodiments of an inspection lamp having two or more LEDs 1801 and associated concave mirrors 1802.

Figure 19:
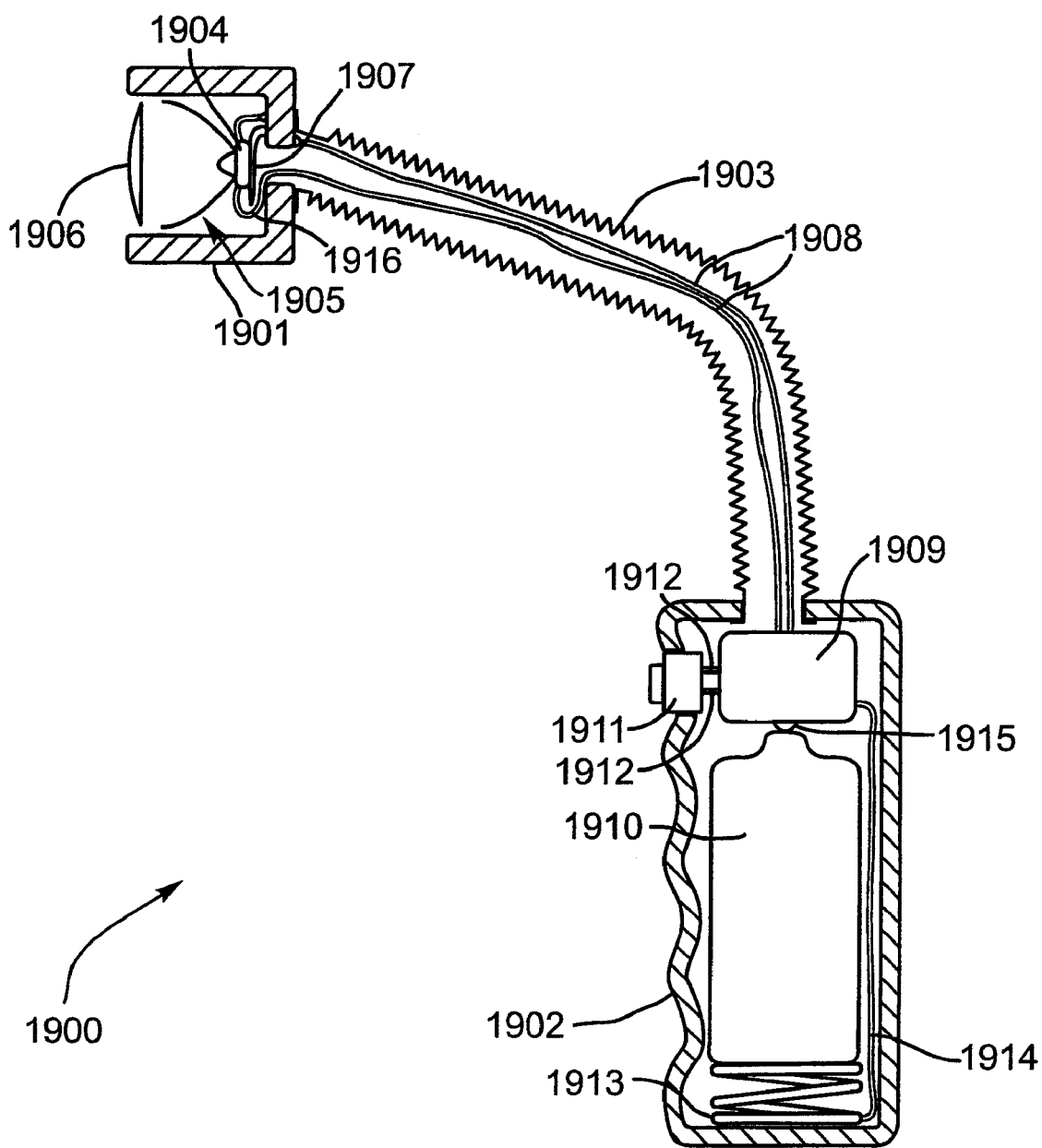
FIG. 19 is a cross sectional side view of a twelfth embodiment of the present invention.

Referring to FIG. 19, a twelfth embodiment of the present invention can be an inspection lamp 1900 comprising a head 1901 and a handle 1902 connected together by a flexible member 1903. Disposed within the head 1901 is at least one LED 1904. A reflector 1905 and/or a lens 1906 may be but are not necessarily provided for collimating the radiation produced by the LED 1904 into a beam. The LED receives power via wires 1908, although if the flexible member 1903 is conductive it may be used in lieu of one of the wires 1908.

The LED 1904 is preferably a high power type that requires or benefits from heatsinking. Heatsinking may be provided by any combination of the head 1901, flexible member 1902 and either or both of the wires 1908. One or more additional wires (not shown) may be provided to conduct heat from the LED 1904 without supplying power to it.

The LED 1904 may be attached to a cap 1907 that has one or more holes 1916 that any of the wires 1908 can pass through. Alternative arrangements are possible, such as mounting the LED 1904 directly to the head 1901.

The LED 1904 preferably has a peak wavelength of 395 to 415 nanometers, so that its radiation is sufficiently visible to visibly illuminate the area being irradiated, but not so visible as to overwhelm the light produced by fluorescent materials to be detected by using the inspection lamp 1900. Alternatively, the LED 1900 can have a shorter peak wavelength since most ultraviolet LEDs produce some visible light. Such a shorter wavelength model of the LED 1904 may have a peak wavelength in the 380 to 395 nanometer range and have some of its main emission band slightly visible, or it may have the long wavelength "tail" of of its main emission band being adequately visible, or it may have visible out-of-band content, or it may contain or have added to it fluorescent material for producing a small amount of visible light. Fluorescent material for producing a small amount of visible light to illuminate the area being irradiated, if used, may be placed anywhere in the head 1904.

Further alternatively, the radiation produced by the inspection lamp 1900 may be essentially invisible, or it may be so visible that viewing glasses or a viewing filter that blocks most of this radiation would be necessary in order to see the fluorescence of fluorescent materials to be detected by using the inspection lamp 1900.

A reflector 1905 may be provided in the head 1901 for purposes such as collimating light from the LED 1904 into a beam. A front lens 1906 is typically but not necessarily provided for any combination of purposes such as filtering the radiation produced by the LED 1904, collimating the radiation from the LED 1904 into a beam, or protecting the LED 1904 or other parts from water, dirt, dust, or impact by foreign objects. Any reflector 1905 is typically but not necessarily of a concave shape such as paraboloidal or ellipsoidal, but may be spherical, conical, of another shape, or of a combination of shapes or comprise zones of different shapes. Any reflector 1905 may be faceted or textured. Any lens 1906 may be planar, biconvex, planoconvex, concavoconvex, biconcave, planoconcave, convexoconcave, a combination of zones of different shapes, or a fresnel version of any of these shapes. Any curvature used on a front lenms 1906 may be spherical shape or an aspheric shape such as paraboloidal, hyperboloidal, or ellipsoidal or a different aspheric shape. Any lens 1906 may be translucent, frosted or textured if diffusing properties are desired for any purpose such as smoothing irregularities in the beam of radiation projected forwards from the head 1901. Any lens 1906 may have filtering characteristics.

The handle 1902 is shown as being in the shape of a pistol grip, but it may be cylindrical or of any other shape.

An LED inspection lamp typically requires current limiting circuitry 1909 for the at least one LED 1904 to operate properly. The circuitry 1909 may comprise one or more resistors, one or more linear regulators, one or more switching regulators, one or more boost converters, or one or more current regulating boost converters. Typically but not necessarily no more than one regulating circuit or boost converter is used.

The current limiting circuit 1909 is shown in the handle 1902 but alternatively it may be located anywhere in or on the inspection lamp 1900.

The inspection lamp 1900 typically but not necessarily has one or more batteries 1910.

The inspection lamp 1900 typically has a switch 1911. The switch 1911 may have wires 1912 connected to it, or it may be combined with the circuitry 1909 into a single assembly. Other arrangements are possible.

The inspection lamp 1900 may, as shown, have a battery spring contact 1913 and a wire 1914 or other conductor connected to the batery spring contact 1913. As shown, the current limiting circuit 1909 may be comprised in a module having a battery contact 1915. Other arrangements are possible.

Any optical filters or filtering lenses used in any embodiment of the present invention may have a filtering dye, be dichroic, or be an interference filter or a colloidal filter.

Any reflectors used in any embodiment of the present invention may have dichroic reflective surfaces for any purpose such as filtering.

Any switches used in any embodiment of the present invention may be momentary, non-momentary or of a kind that is usable both as a momentary switch and as a non-momentary switch.

Any batteries used in any embodiment of the present invention may be rechargeable or non-rechargeable. Non-rechargeable batteries used in any embodiment of the present invention may be zinc carbon, alkaline, mercury, silver oxide, lithium or any other kind of non-rechargeable battery. Rechargeable batteries used in any embodiment of the present invention may be lead acid, nickel cadmium, nickel metal hydride, lithium ion, or any other rechargeable kind of battery. Any embodiment of the present invention that uses rechargeable batteries may further comprise a charging jack. Any embodiment of the present invention that uses rechargeable batteries may further comprise circuitry used in recharging of the batteries. Any embodiment of the present invention that uses rechargeable batteries may further comprise a charger.

Any embodiment of the present invention may further comprise means to accept power from an external source, whether or not it also uses any batteries.

Any embodiment of the present invention may have a thermal cutout device to prevent overheating of any LEDs or any other parts.

Any embodiment of the present invention may have indicator lamps for purposes such as indicating any status of any batteries or indicating that the LEDs are producing radiation. Fluorescent material may be added to an inspection lamp to give visible indication that fluorescence-causing radiation is being produced.

Any embodiment of the present invention may further comprise means to achieve strobing of any LEDs, since doing so may achieve greater visibility of fluorescent materials to be detected.

Any current limiting circuits used in any embodiment of the present invention may comprise one or more integrated circuits. Any current limiting circuits used in any embodiment of the present invention may comprise at least one integrated circuit and at least one discrete component. Any current regulating circuit used in any embodiment of the present invention may be achieved with one or more discrete components and no integrated circuits.

It will be understood by those skilled in the art that this description is made with reference to the preferred embodiments thereof and that it is possible to make other embodiments employing the principles of the invention which fall within its spirit and scope as defined by the following claims.

We claim:

1. A inspection lamp, comprising:
   a) a head section that contains one or more light emitting diodes that emit radiation, a majority of which radiation is directed generally rearwards within the head section,
   b) a handle section such that the lamp can be hand held, and
   c) a concave reflector for receiving and collimating a majority of the rearwardly directed radiation into a beam,
   wherein at least one light emitting diode produces radiation that is suitable for causing fluorescence of visibly fluorescent materials.

2. The lamp of claim 1, wherein the reflector comprises a transparent optic to collimate the radiation into a beam, wherein the transparent optic uses total internal reflection for at least part of the collimation of the beam.

3. The lamp of claim 1, further comprising a lens forward of the reflector in a position so that the rearwardly directed radiation does not pass through the lens, the lens having a textured surface to act as a diffuser for the collimated beam.

4. The lamp of claim 2, further comprising a lens forward of the transparent optic, the lens having a textured surface to act as a diffuser for the collimated beam.

5. The lamp of claim 1, wherein the at least one LED has a peak wavelength in a range of 395 to 415 nanometers.

6. The lamp of claim 1, wherein the at least one LED has a peak wavelength of approximately 450 nanometers.

7. The lamp of claim 1, wherein the at least one LED has a peak wavelength in a range of 460 to 505 nanometers.

8. The lamp of claim 1, wherein the at least one LED has a peak wavelength below 395 nanometers.

9. The lamp of claim 1, wherein the at least one LED has a peak wavelength at 380 nanometers or below.

10. The lamp of claim 1, further comprising: a boost converter suitable for operating at least one LED in the lamp using a battery that has a voltage less than that required to operate the at least one LED.

11. The lamp of claim 10, wherein the boost converter comprises:
    an inductor, a diode, and a transistor arranged so that current flowing through said inductor is intermittently increased as a result of said transistor being in a conductive state and forced to decrease and flow through said LED when said transistor is in a nonconductive state,
    a current sensing resistor that any current flowing through the inductor always flows through, and
    a comparator that switches said transistor alternatively into a conductive state and a nonconductive state according to the magnitude of the current that is flowing through said current sensing resistor.

12. The lamp of claim 10, wherein the boost converter further comprises means to shut itself down if the power supply voltage is excessively low.

13. The lamp of claim 10, wherein the boost converter further comprises means to shut itself down if its output voltage becomes excessive as a result of failure of an LED in the lamp to conduct current.

14. The lamp of claim 10, wherein the boost converter further comprises means to essentially regulate the amount of power that it delivers to an LED should the voltage of the power supply that said boost converter receives power from vary within a range of voltages that said power supply typically has.

15. The lamp of claim 10, further comprising a current regulator to regulate the amount of current flowing to the at least one LED.

16. The lamp of claim 15, wherein the current regulator is a switching current regulator.

17. The lamp of claim 10, further comprising means to strobe any one of the at least one LEDs.

18. The lamp of claim 1, further comprising a boost converter that comprises:
    an inductor, a diode, and a transistor arranged so that current flowing through said inductor is intermittently increased as a result of said transistor being in a conductive state and forced to decrease and flow through said LED when said transistor is in a nonconductive state, and
    an oscillator that alternatively switches said transistor into its conductive state and its nonconductive state.

19. The lamp of claim 1, further comprising a boost converter that comprises:
    an inductor, a diode, and a transistor arranged so that current flowing through said inductor is intermittently increased as a result of said transistor being in a conductive state and forced to decrease and flow through said LED when said transistor is in a nonconductive state, a current sensing resistor that any current flowing through said inductor always flows through, and a linear timer integrated circuit arranged to alternately switch said transistor into its conductive and nonconductive states according to the magnitude of the current through said current sensing resistor.

20. An inspection lamp, comprising: at least one LED and a boost converter suitable for operating at least one LED in the lamp using a battery that has a voltage less than that required to operate the at least one LED, wherein at least one LED produces radiation that is suitable for causing fluorescence of visibly fluorescent materials.

21. An inspection lamp, comprising at least one LED that produces radiation that is suitable for causing fluorescence of visibly fluorescent materials and a boost converter that comprises:

an inductor, a diode, and a transistor arranged so that current flowing through said inductor is intermittently increased as a result of said transistor being in a conductive state and forced to decrease and flow through said LED when said transistor is in a nonconductive state, and an oscillator that alternatively switches said transistor into its conductive state and its nonconductive state.

22. An inspection lamp, comprising at least one LED that produces radiation that is suitable for causing fluorescence of visibly fluorescent materials and a boost converter that comprises:

an inductor, a diode, and a transistor arranged so that current flowing through said inductor is intermittently increased as a result of said transistor being in a conductive state and forced to decrease and flow through said LED when said transistor is in a nonconductive state, a current sensing resistor that any current flowing through said inductor always flows through, and a linear timer integrated circuit arranged to alternately switch said transistor into its conductive and nonconductive states according to the magnitude of the current through said current sensing resistor.

23. An inspection lamp, comprising:

a) a head section that contains one or more light emitting diodes that emit radiation, a majority of which radiation is directed generally rearwards within the head section, b) a handle section such that the lamp can be hand held, and c) a concave reflector for receiving and collimating a majority of the rearwardly directed radiation into a beam, wherein at least one light emitting diode produces radiation that is suitable for causing fluorescence of visibly fluorescent materials, and wherein the head section conducts heat from the one or more light emitting diodes.

24. An inspection lamp, comprising:

a) a head section that contains one or more light emitting diodes that emit radiation, a majority of which radiation is directed generally rearwards within the head section, b) a handle section such that the lamp can be hand held, and c) a concave reflector for receiving and collimating a majority of the rearwardly directed radiation into a beam, wherein at least one light emitting diode produces radiation that is suitable for causing fluorescence of visibly fluorescent materials, wherein the reflector comprises a transparent optic to collimate the radiation into a beam, and wherein the transparent optic uses total internal reflection for at least part of the collimation of the beam.

25. The inspection lamp of claim 24 wherein the head section conducts heat from the one or more light emitting diodes.

* * * * *